(12) United States Patent
Sol

(10) Patent No.: US 9,324,244 B1
(45) Date of Patent: Apr. 26, 2016

(54) DISTRIBUTED MULTI-NODAL OPERANT CONDITIONING SYSTEM AND METHOD

(76) Inventor: David Sol, Calabasas, CA (US)

( * ) Notice: Subject to any disclaimer, the term of this patent is extended or adjusted under 35 U.S.C. 154(b) by 590 days.

(21) Appl. No.: 12/780,867

(22) Filed: May 15, 2010

(51) Int. Cl.
*G09B 19/00* (2006.01)
*A61B 5/16* (2006.01)
*G09B 9/052* (2006.01)

(52) U.S. Cl.
CPC . *G09B 19/00* (2013.01); *A61B 5/16* (2013.01); *G09B 9/052* (2013.01)

(58) Field of Classification Search
USPC .................................. 434/236–238; 119/720
See application file for complete search history.

(56) References Cited

U.S. PATENT DOCUMENTS

| | | | |
|---|---|---|---|
| 3,998,209 A | 12/1976 | Macvaugh | |
| 4,640,267 A | 2/1987 | Lawson | |
| 5,082,002 A * | 1/1992 | Silverman et al. | 600/594 |
| 5,243,998 A * | 9/1993 | Silverman et al. | 600/595 |
| 5,406,957 A * | 4/1995 | Tansey | 600/545 |
| 5,871,518 A | 2/1999 | Blum | |
| 6,402,520 B1 * | 6/2002 | Freer | 434/236 |
| 6,582,380 B2 * | 6/2003 | Kazlausky et al. | 600/595 |
| 6,585,521 B1 * | 7/2003 | Obrador | 434/236 |
| 6,699,043 B2 * | 3/2004 | Ho et al. | 434/236 |
| 7,248,171 B2 * | 7/2007 | Mishelevich | 340/573.1 |
| 7,380,518 B2 * | 6/2008 | Kates | 119/72 |
| 7,434,541 B2 * | 10/2008 | Kates | 119/720 |
| 7,580,742 B2 * | 8/2009 | Tan et al. | 600/544 |
| 7,580,798 B2 * | 8/2009 | Brunner et al. | 702/19 |
| 7,882,135 B2 * | 2/2011 | Brunner et al. | 707/791 |
| 2001/0029319 A1 * | 10/2001 | Kazlausky et al. | 600/300 |
| 2002/0021220 A1 | 2/2002 | Dreyer | |
| 2002/0086272 A1 * | 7/2002 | Ho et al. | 434/236 |
| 2003/0118974 A1 * | 6/2003 | Obrador | 434/236 |
| 2003/0199945 A1 * | 10/2003 | Ciulla | 607/48 |
| 2004/0144076 A1 | 7/2004 | Barker | |
| 2004/0230549 A1 * | 11/2004 | Freer et al. | 706/61 |
| 2005/0235925 A1 * | 10/2005 | Lalor | 119/719 |
| 2005/0280544 A1 * | 12/2005 | Mishelevich | 340/573.1 |
| 2006/0011146 A1 * | 1/2006 | Kates | 119/719 |
| 2006/0196445 A1 * | 9/2006 | Kates | 119/719 |
| 2006/0201436 A1 * | 9/2006 | Kates | 119/72 |
| 2007/0048707 A1 * | 3/2007 | Caamano et al. | 434/236 |
| 2007/0185697 A1 * | 8/2007 | Tan et al. | 703/11 |
| 2008/0193010 A1 * | 8/2008 | Eaton et al. | 382/159 |
| 2008/0282988 A1 * | 11/2008 | Bloksberg | 119/51.02 |
| 2008/0282993 A1 | 11/2008 | Hoehn | |
| 2008/0306980 A1 * | 12/2008 | Brunner et al. | 707/102 |
| 2010/0106743 A1 * | 4/2010 | Brunner et al. | 707/780 |
| 2010/0275851 A1 * | 11/2010 | Yin | 119/51.02 |

* cited by examiner

*Primary Examiner* — Robert J Utama

(57) ABSTRACT

A multi-nodal distributed operant conditioning system and method consisting of a user node and one or more networked subject nodes. A user audience at a user node engages in operant conditioning with a subject at a networked subject node by observing real time image data of the subject and effecting operant conditioning signals to the subject in response to operantly offered behaviors by the subject. The multi-nodal, distributed nature of the embodiments provides for uses by a user audience in educational, entertainment, or therapeutic behavioral modification settings.

27 Claims, 32 Drawing Sheets

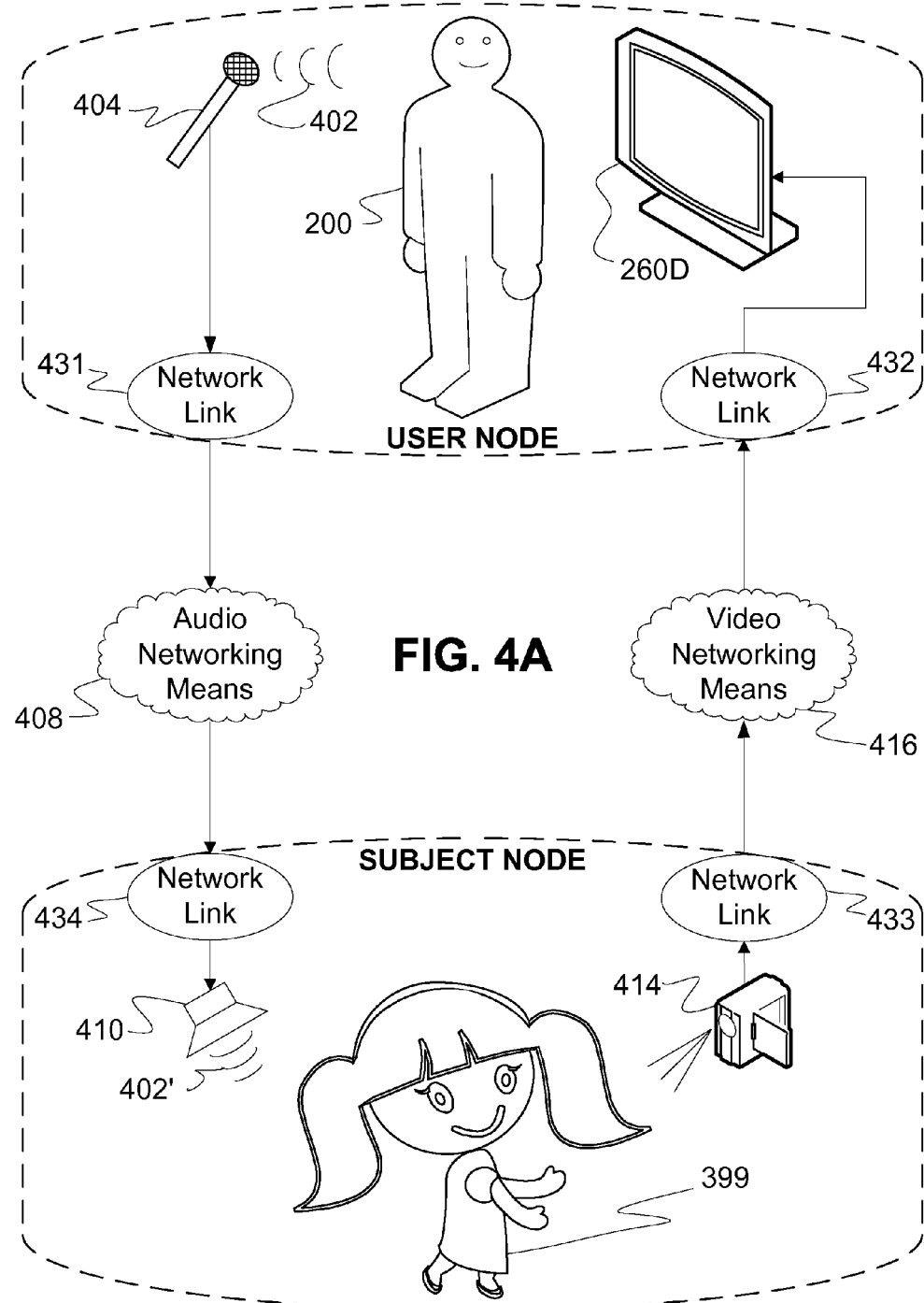

FIG. 4B
FIG. 4C
FIG. 4D
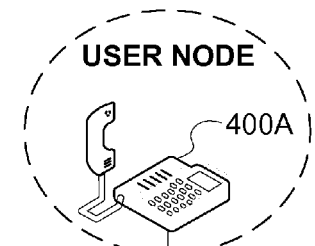
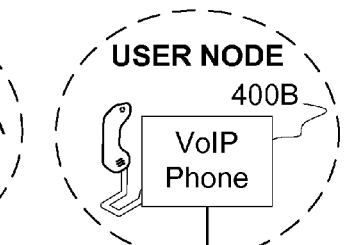
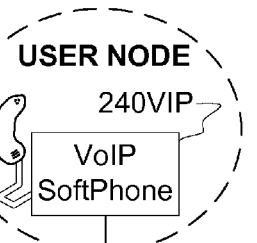
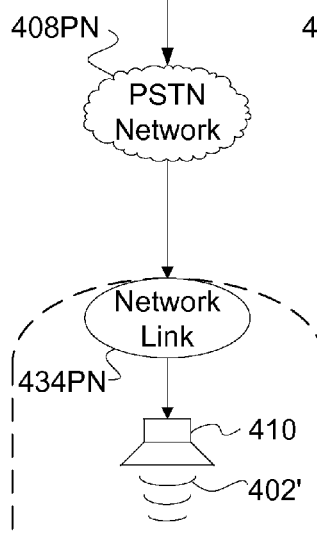
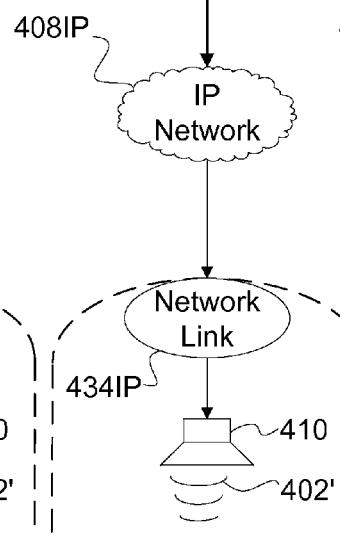
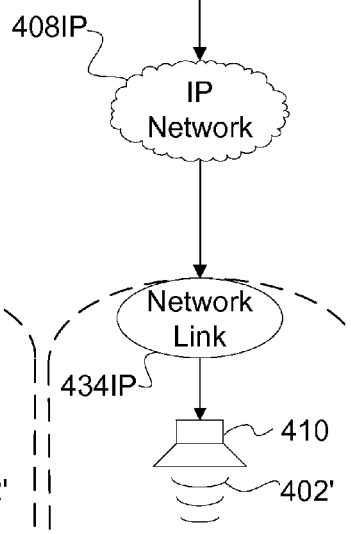
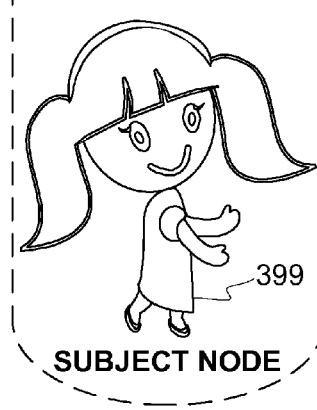
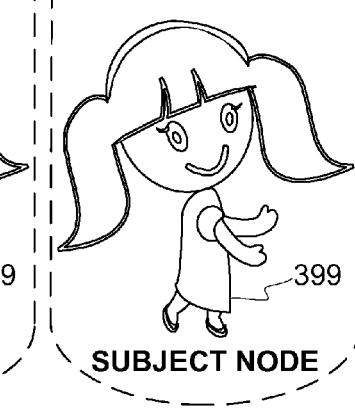
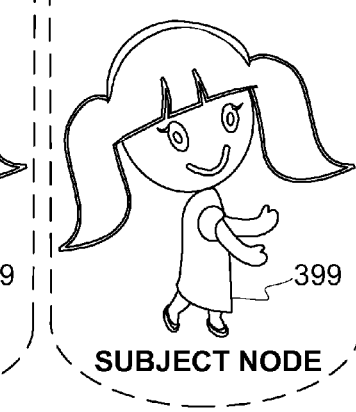

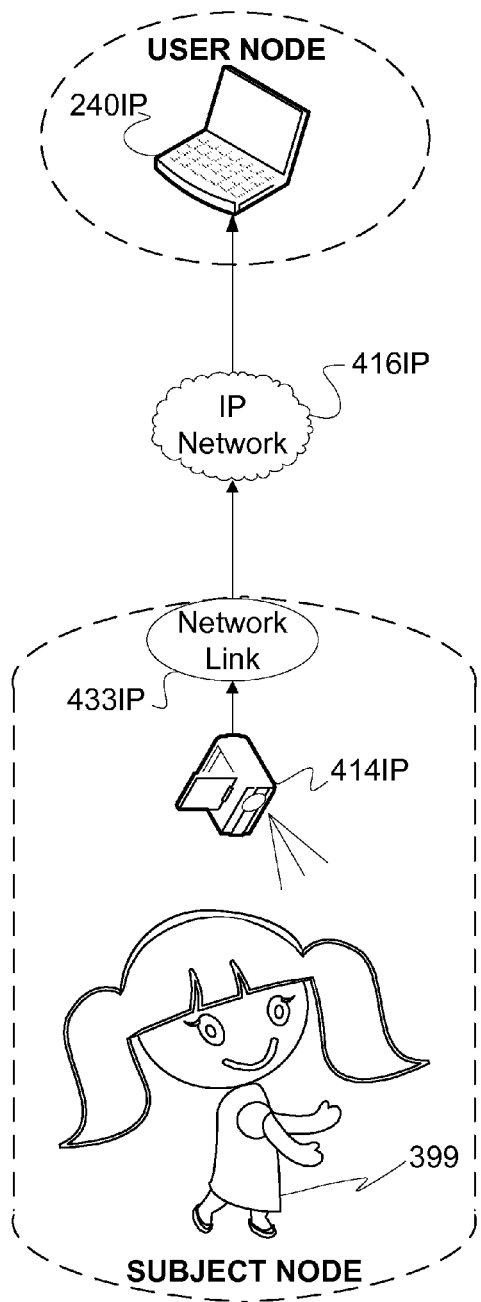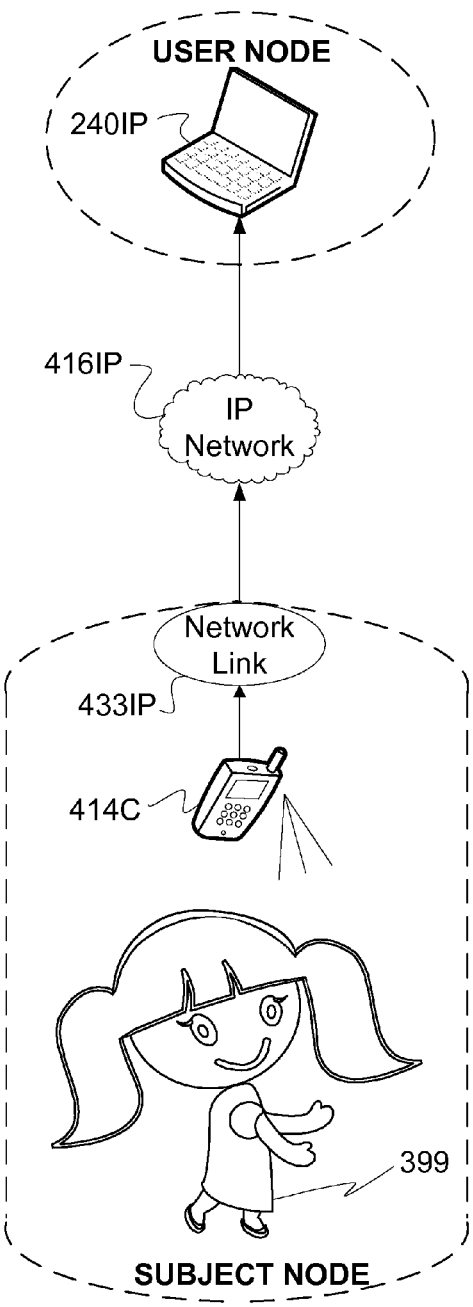

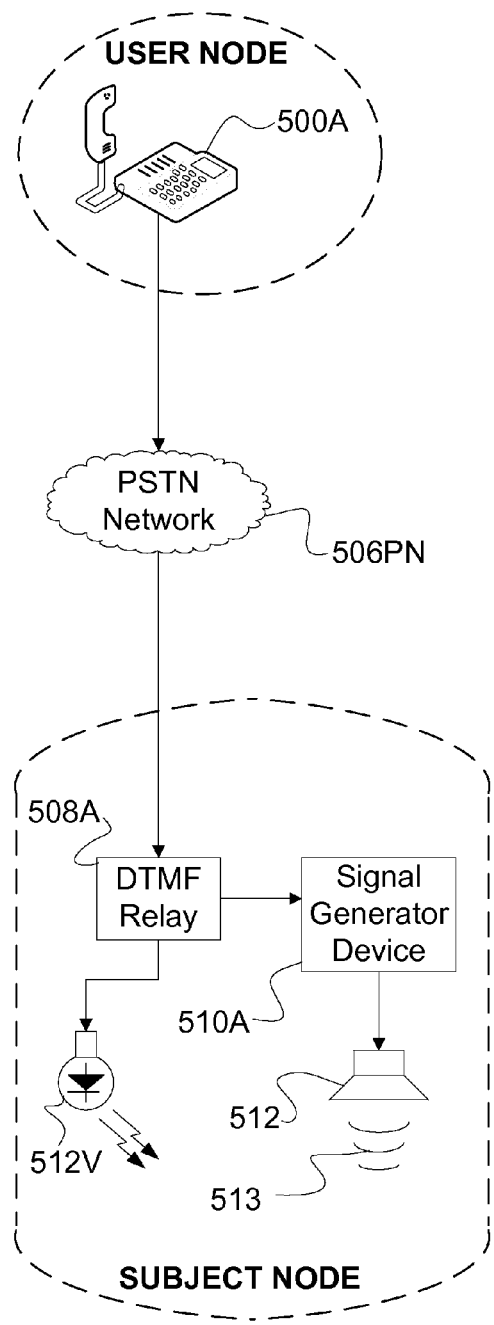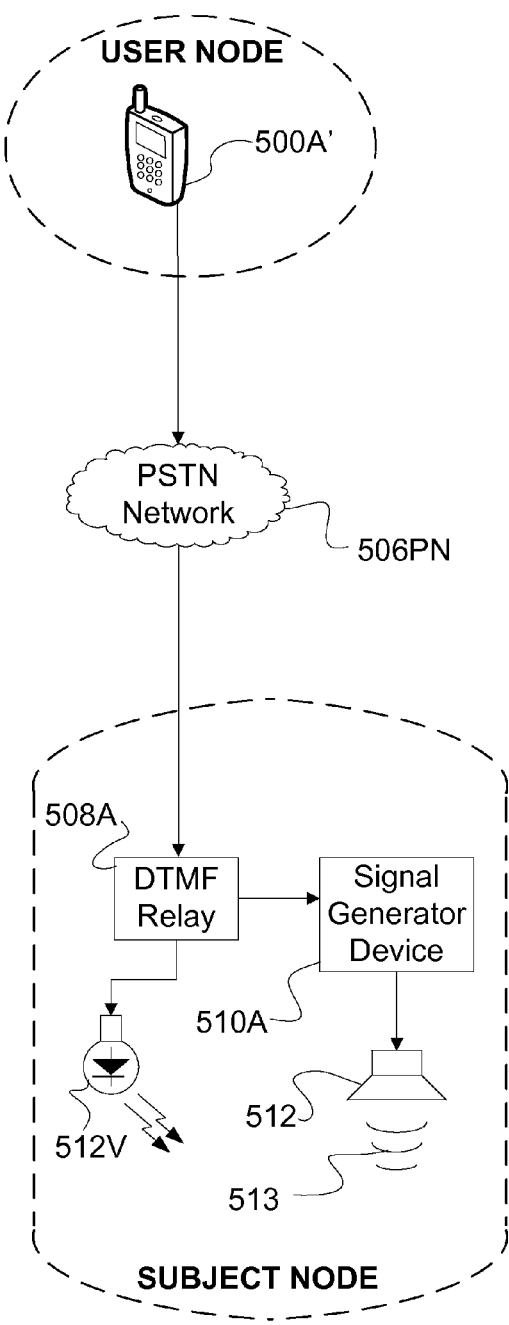

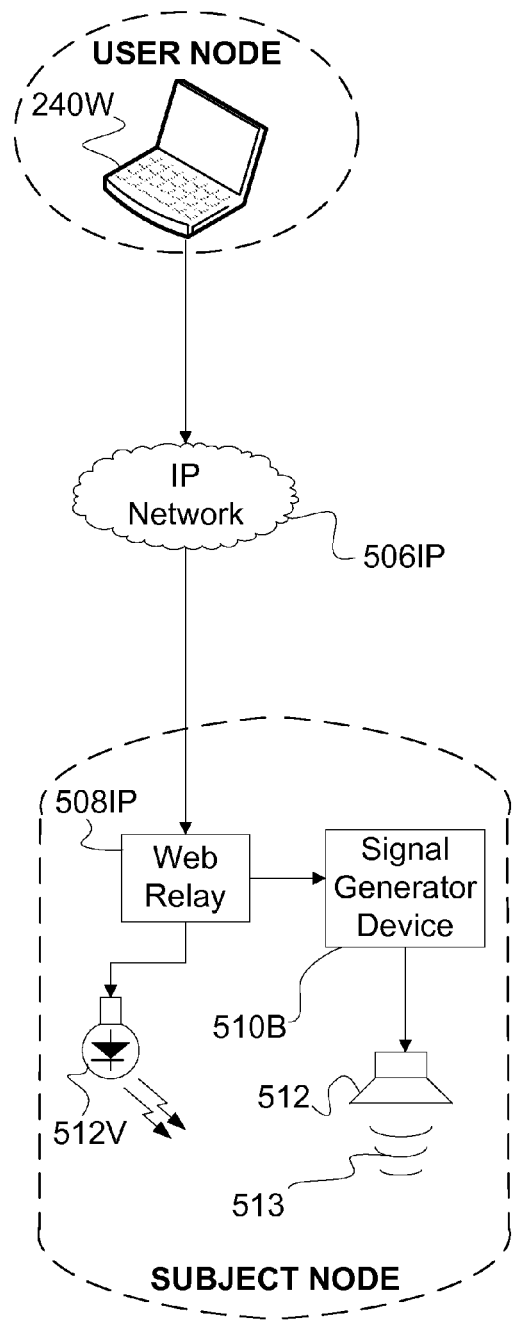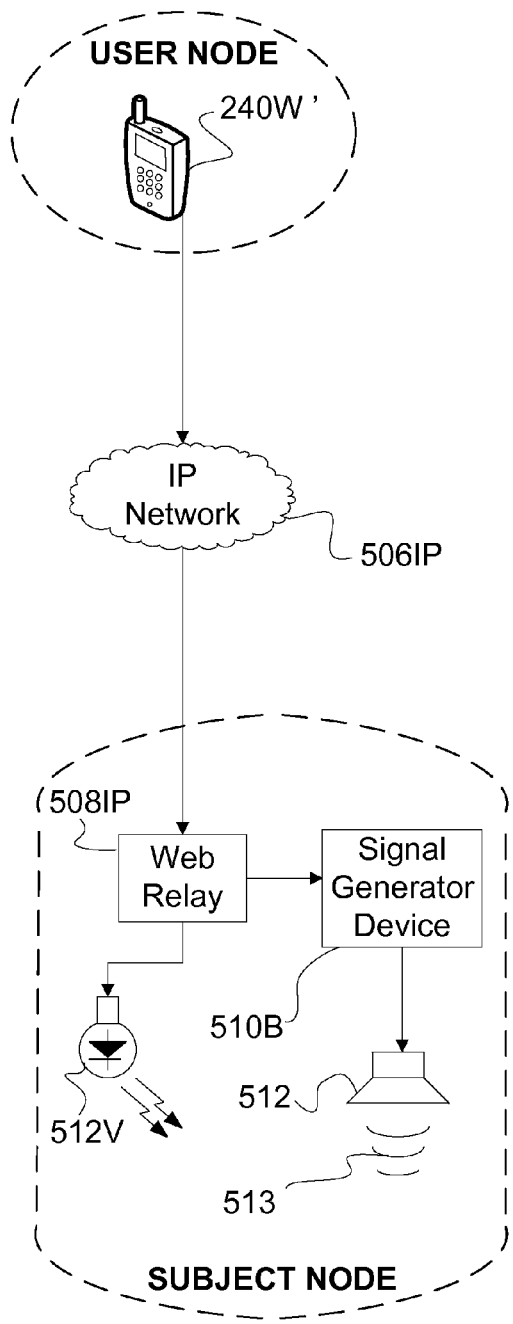

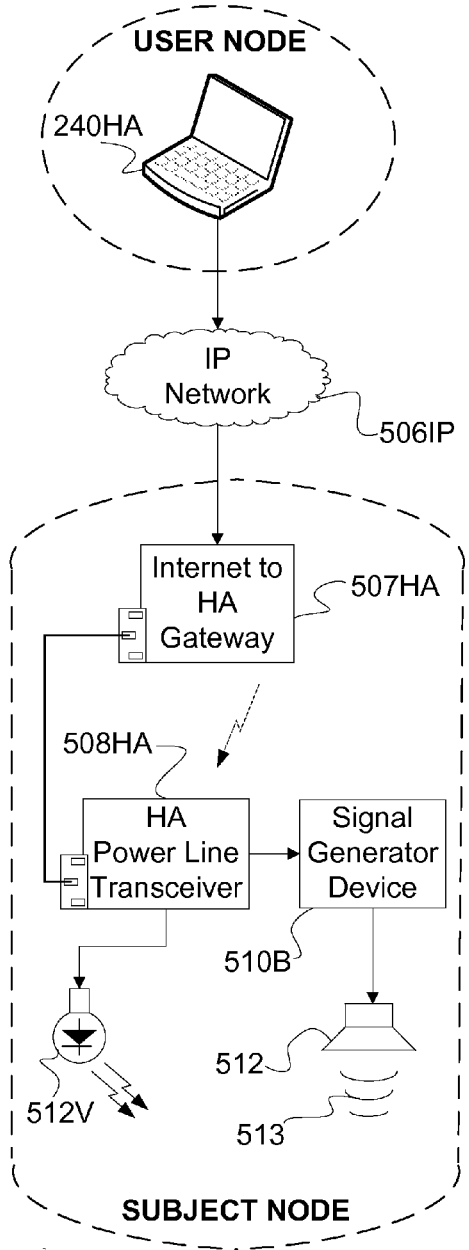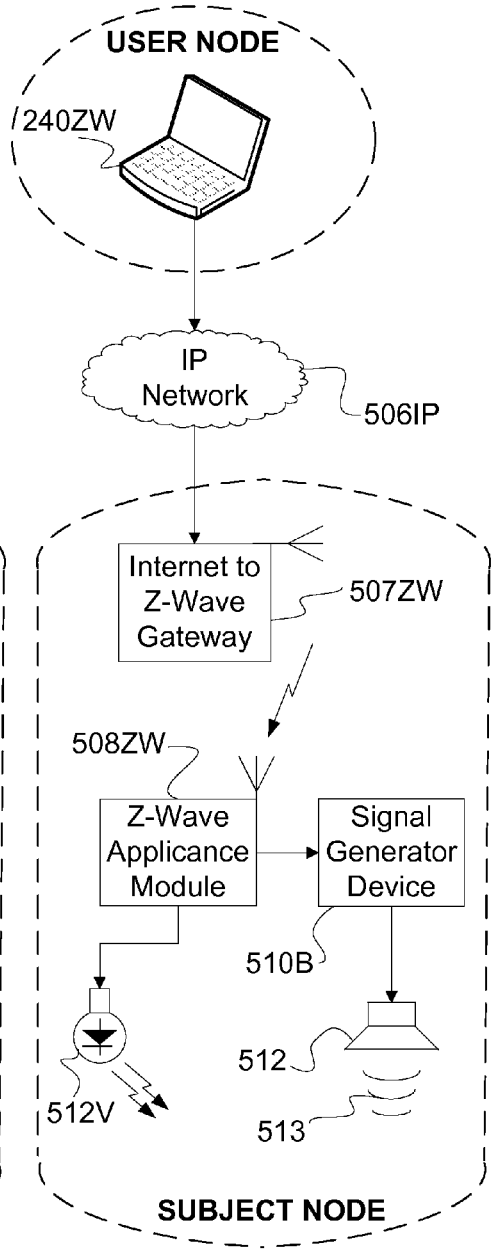

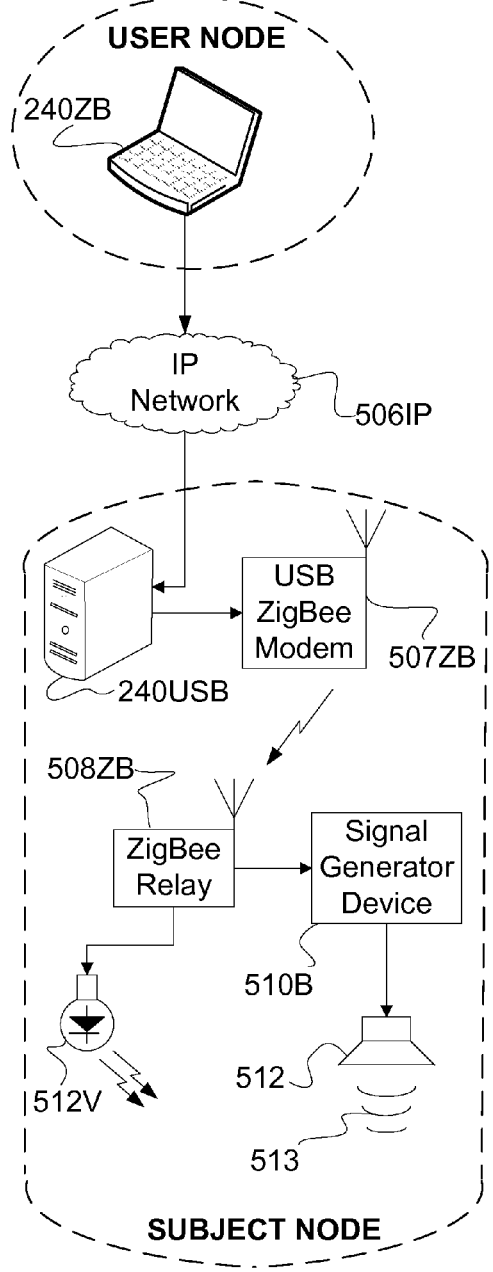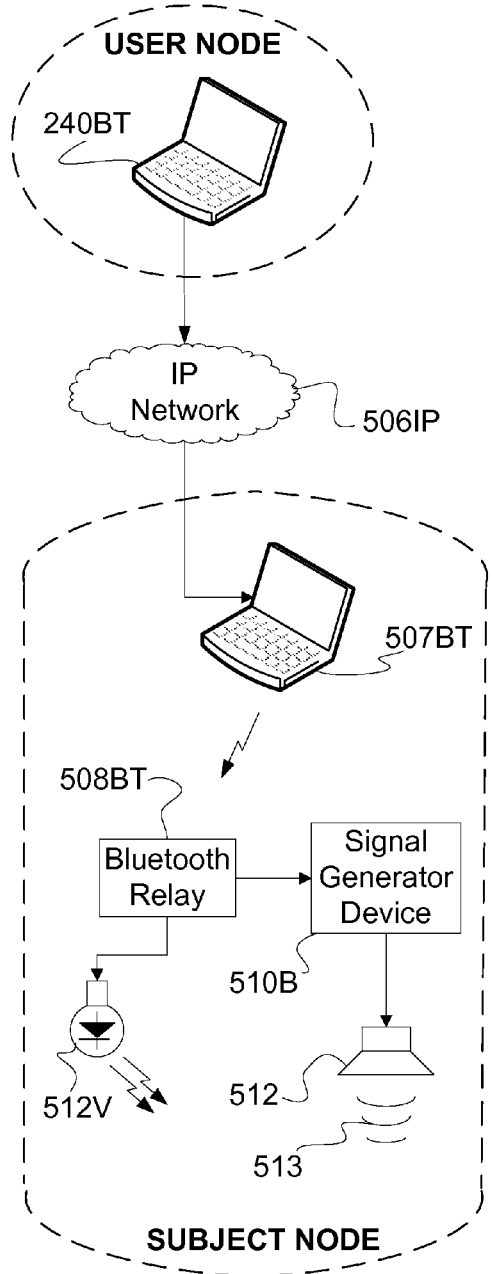

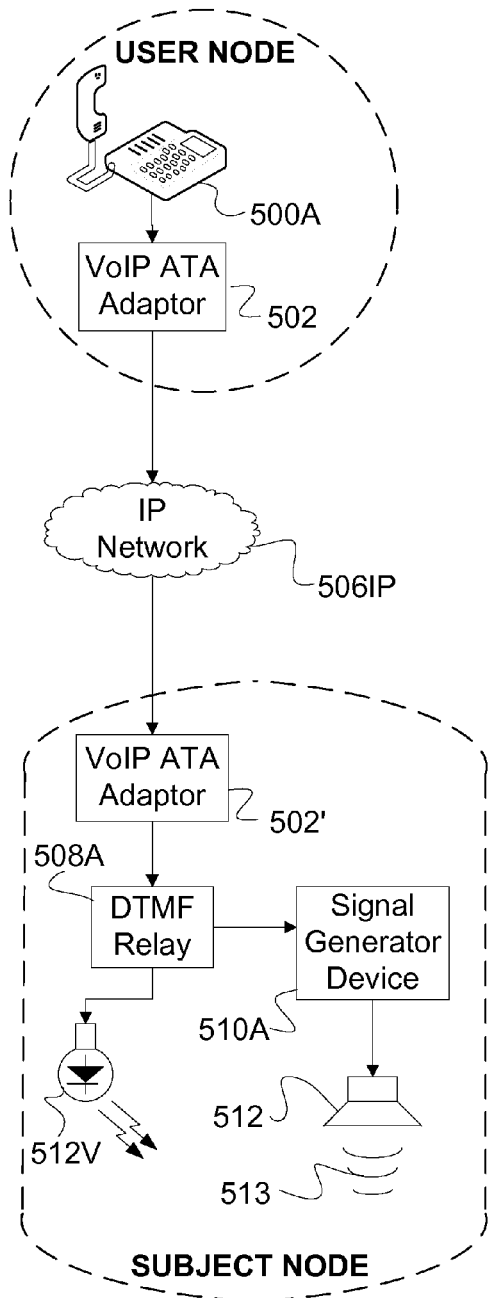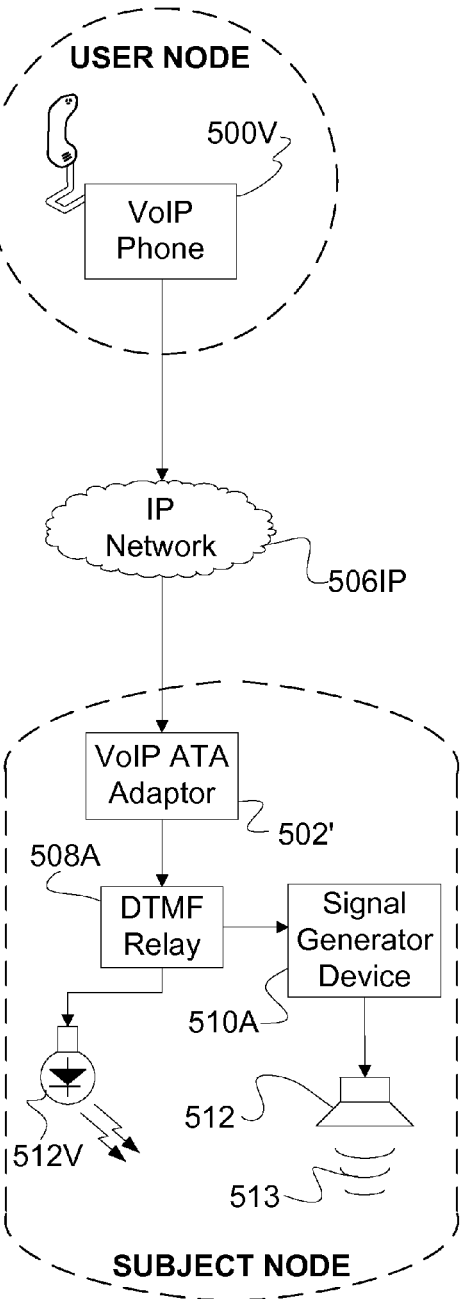

FIG. 6A FIG. 6B FIG. 6C FIG. 6D
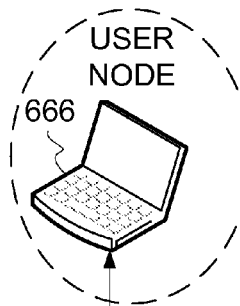
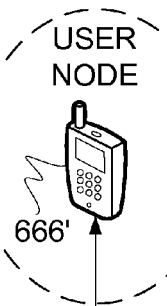
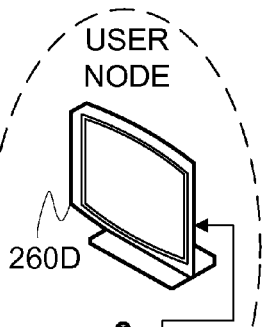
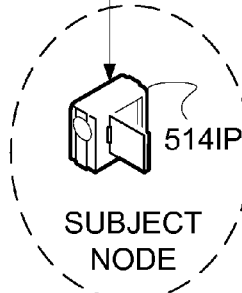
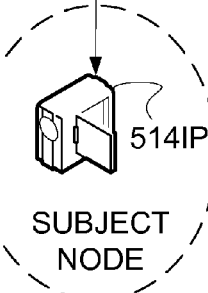
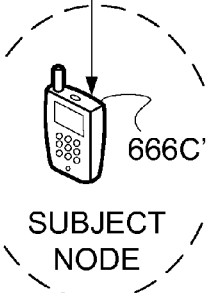
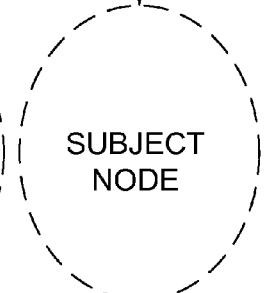

DISTRIBUTED MULTI-NODAL OPERANT CONDITIONING SYSTEM AND METHOD

TECHNICAL FIELD

The embodiments of the present invention relate generally to operant conditioning.

BACKGROUND ART

The following is a tabulation of some prior art that presently appears relevant:

| U.S. Pat. | | | |
|---|---|---|---|
| Pat. No. | Kind Code | Issue Date | Patentee |
| 5,871,518 | | Feb. 16, 1999 | Blum |
| 5,243,998 | | Sep. 14, 1993 | Silverman et al. |
| 5,082,002 | | Jan. 21, 1992 | Silverman et al. |
| 4,640,267 | | Feb. 3, 1987 | Lawson |
| 3,998,209 | | Dec. 21, 1976 | Macvaugh |

| U.S. patents application Publications | | | |
|---|---|---|---|
| Publication Number | Kind Code | Publication Date | Applicant |
| 2008/0282993 | A1 | Nov. 20, 2008 | Hoehn |
| 2004/0144076 | A1 | Jul. 29, 2004 | Barker |
| 2002/0021220 | A1 | Feb. 21, 2002 | Dreyer |

OTHER PUBLICATIONS

Skinner, B. F., "The Behavior of Organisms", Copley Publishing Group, 1938

Pryor, Karen, "Don't Shoot the Dog!", Bantam Books, 1985, 1999

Petruzzellis, Tom, "Telephone Projects for the Evil Genius", McGraw-Hill, 2009

Ledford, Jerri, "25 Home Automation Projects for the Evil Genius", McGraw-Hill, 2007

In psychology and education, learning theories attempt to describe how people and organisms learn. Behavioral learning theories describe two types of learning: classical conditioning and operant conditioning.

The psychological principles of classical conditioning had its origins in the study of reflexes, based on the work of Ivan Pavlov, a Russian physiologist who studied salivary responses in dogs. Classical conditioning, also referred to as Pavlovian or respondent conditioning, is an associative type of learning, in which classically conditioned behaviors are reflexive to environmental stimuli.

The psychological principles of operant conditioning were first developed and studied by psychologists Edward Thorndike (1874-1949) and later refined and published by B. F. Skinner (1904-1990). Operant conditioning, also referred to as Skinnerian conditioning, occurs where voluntary behaviors by a subject operate on the environment as opposed to the environment operating on the subject.

Blum (U.S. Pat. No. 5,871,518 titled "Smoking Cessation Lighter and Method") describes a lighter for tobacco products which suppresses the urge to smoke by operant conditioning, delivering a shock to the user's hand.

Silverman et al. (U.S. Pat. No. 5,243,998 titled "Automatic Operant Conditioning System" and U.S. Pat. No. 5,082,002 titled "Automatic Operant Conditioning System Especially for Scoliosis") describes the operant conditioning of subjects using biofeedback from a device connected to the subject to measure a condition such as posture with the results of both negative and positive reinforcements based on the measurements.

Lawson (U.S. Pat. No. 4,640,267 titled "Method and Apparatus for Nondetrimental Reduction of Infant Crying Behavior") describes an apparatus for operant conditioning of the crying of an infant with positive reinforcement contingent upon the cessation of vocal behavior exceeding predetermined audible levels.

Macvaugh (U.S. Pat. No. 3,998,209 titled "Snoring Deconditioning System and Method") describes a snore deconditioning system including both Pavlovian (respondent) and Skinnerian (operant) conditioning, encompassing awakening the snorer and application of aversive stimuli.

Hoehn (U. S. Patent Application No. 2008/0282993 titled "Animal Training Device and Method") describes a training device to alert a human that an animal needs to urinate or defecate, and its use along with treats as an operant conditioning method.

Barker (U. S. Patent Application No. 2004/0144076 titled "Girth Monitor") describes a decorative chain with an adjustable catch worn continuously about a person's waist, and that variations in perceived waist pressure provide operant conditioning feedback.

Dreyer (U. S. Patent Application No. 2002/0021220 titled "Method and Apparatus for Toilet Training and Related Wetness Sensing Material") describes an apparatus for generating a stimulus when a child's diaper is wet or soiled and transferring the stimulus to the use of a toilet as a means of operant conditioning.

BRIEF DESCRIPTION OF THE DRAWINGS

The present invention is illustrated by way of example and not limitation in the figures of the accompanying drawings, in which:

FIG. 4A shows finer detail of the example embodiment.

FIGS. 4B, 4C & 4D illustrate example embodiments of audio networking means between user and subject nodes.

FIGS. 4E & 4F illustrate example embodiments of video networking means between user and subject nodes.

FIGS. 5B-5K show additional example embodiments communicating signals from the user node to the subject node through signal networking means:

FIG. 5B shows the use of a DTMF (Dual Tone Multi-Frequency) telephone with the Public Switched Telephone Network (PSTN).

FIG. 5C shows the use of a DTMF capable cellular phone with the PSTN network.

FIG. 5D shows the use of a computer with the IP (Internet Protocol) network.

FIG. 5E shows the use of a web enabled cellular phone with the IP network.

FIGS. 5F, 5G, 5H & 5I show additional example embodiments for use where the subject node may lack internet access throughout.

FIGS. 5J & 5K show the use of VoIP (Voice over Internet Protocol) over the internet.

FIGS. 6A, 6B, 6C & 6D show additional example embodiments of audio-visual networking means over the internet from user to subject nodes.

DETAILED DESCRIPTION

Introduction—Glossary

Figure 1:
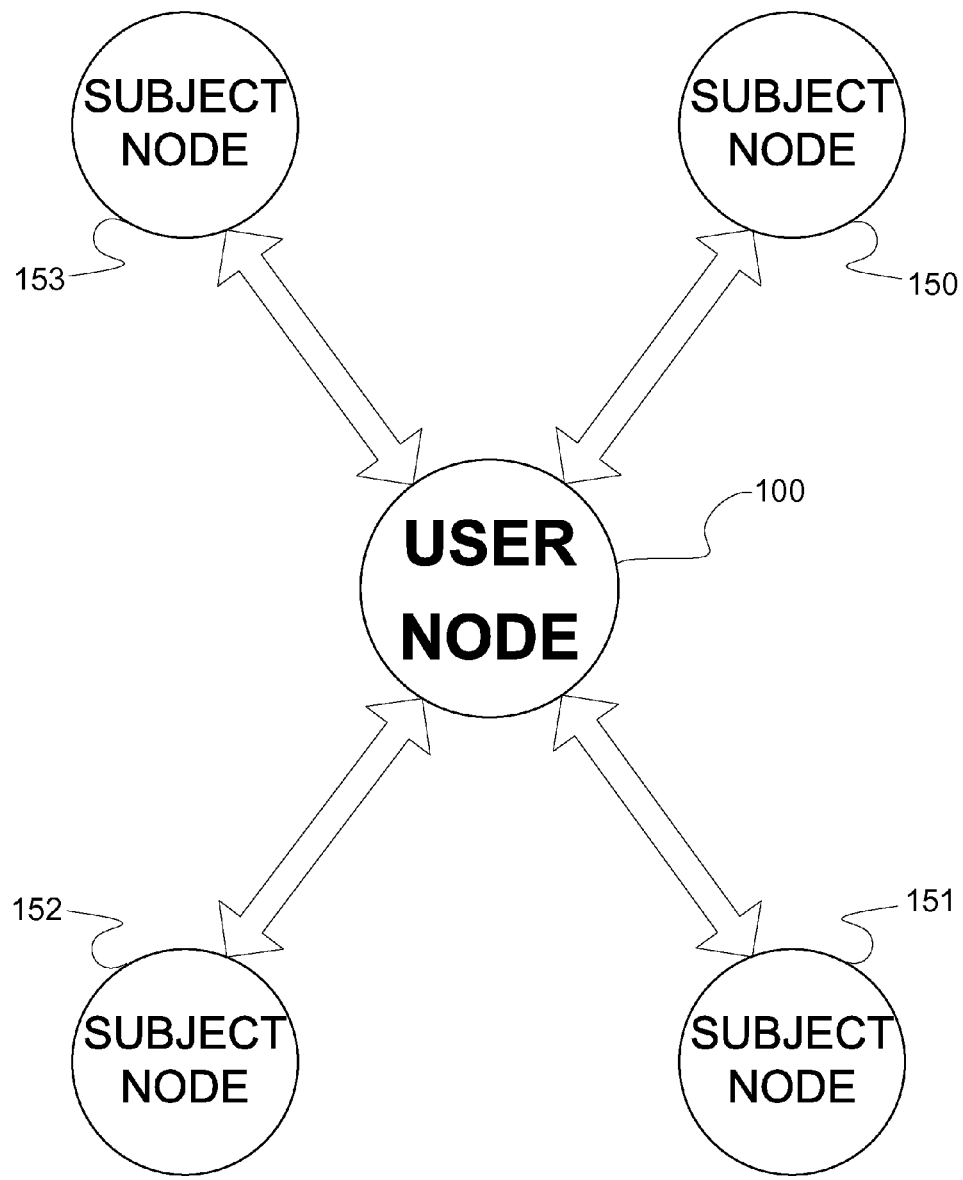
FIG. 1 is a high-level view of an example distributed operant conditioning system, showing a user node in communication with multiple subject nodes.

Conditioning—In the field of psychology, a process of learning, training, habituation, or behavior modification in subjects.

Classical conditioning—Also called respondent conditioning, or Pavlovian conditioning, the conditioning of behaviors which are reflexive responses to stimuli from the environment.

Operant conditioning—A type of learning in which the likelihood of a particular behavior occurring in the future increases or decreases based on the consequences following the behavior. Unlike classical conditioning, the subject offers behaviors voluntarily, not reflexively. In so doing the subject operates on the environment (i.e., emitting behaviors), as opposed to the environment operating on the subject (i.e., eliciting behaviors).

Reinforcement—A consequence to a behavior that causes the likelihood of the behavior occurring in the future to increase.

Positive reinforcement—A consequence to a behavior which is the presentation (i.e., addition) of something favorable or pleasant, thereby increasing the likelihood of that behavior occurring in the future.

Negative reinforcement—A consequence to a behavior which is a removal (i.e., subtraction) of an aversive or unpleasant stimulus, thereby increasing the likelihood of that behavior occurring in the future.

Punishment—A consequence to a behavior that causes the likelihood of the behavior occurring in the future to decrease.

A punishment, like reinforcement, is termed positive (i.e., something added or presented) or negative (i.e., something subtracted or removed).

Primary reinforcer—(Or Primary positive reinforcer, more precisely as used herein unless denoted otherwise)—Also known as an unconditioned reinforcer.

Unconditioned reinforcer—Something always wanted by a subject, without learning or conditioning. For example: food, water, praise, petting, or the opportunity to play with a favorite toy.

Conditioned reinforcer—(Or Conditioned positive reinforcer, more precisely as used herein unless denoted otherwise)—Also known as a secondary reinforcer, it signals that a primary reinforcer is coming through the subject having learned to associate the conditioned reinforcer with the primary reinforcer. A perceptible stimulus from any sensory mode can become a conditioned reinforcer (e.g., light, sound, smell, tactile, etc.). One example of a conditioned reinforcer for humans is money; another is a school bell signaling recess.

In operant conditioning a conditioned reinforcer can serve as a marker signal.

Marker signal—Also known a bridge or bridging signal, it is a precisely timed conditioned reinforcer, a signal to an subject or organism (a sound, light, gesture or the like) containing the information that a primary reinforcer is coming as a consequence of the behavior the subject was performing at the moment of the signal. Some examples are the voiced phrase "Good Boy" or "Good Girl" or the more precise and distinctive sounds of a metallic clicker, whistle, buzzer or the like. Marker signals serve as event markers, bridging time between a marked behavior event and the eventual reinforcement of that behavior.

Shaping—Training a behavior with successive approximation towards a goal. Voluntary actions by the subject which tend towards or increasingly approximate a given target behavior are successively reinforced with the marker signal until the subject has reached the target behavior.

Variable reinforcement—Delivery of the primary reinforcer on a variable schedule as opposed to following every marker signal with the food treat. The element of randomness is known to increase the subject's level of interest and excitement, particularly when the amount and/or type of food treat is varied in such a way that occasionally it is a highly desired "jackpot" to the subject. This unpredictability yields inherently surprising and unexpected results. The subject can get another cue instead of the primary reinforcer, which can lead to building behavior chains.

Command—In traditional training, a command tells a subject what to do. A command may often be followed by an aversive stimulus if the command is not followed. For example, the command "Halt" may be followed by a jerk on a leash or pressure on a bit or harness if not obeyed. The command in traditional training is contrasted with the use of a cue as used in operant conditioning.

Cue—A Cue as used in operant conditioning is an indicator to the subject of an opportunity to earn reinforcement by the subject's own voluntary actions. The cue is some particular stimulus such as a spoken word, hand gesture, or other perceptible signal which identifies to a subject exactly which previously learned behavior will earn positive reinforcement in response to this particular cue at this particular time. From the subject's point of view since the cue is a green light to earn positive reinforcement, it is a desirable thing and so each cue in and of itself becomes a conditioned reinforcer.

Cue control—A behavior is under cue control when the subject voluntarily offers the behavior in response to the cue, and only in response to the cue. This can be achieved by reinforcing the behavior only when given in response to the cue.

Description of the Embodiments

Figure 2:
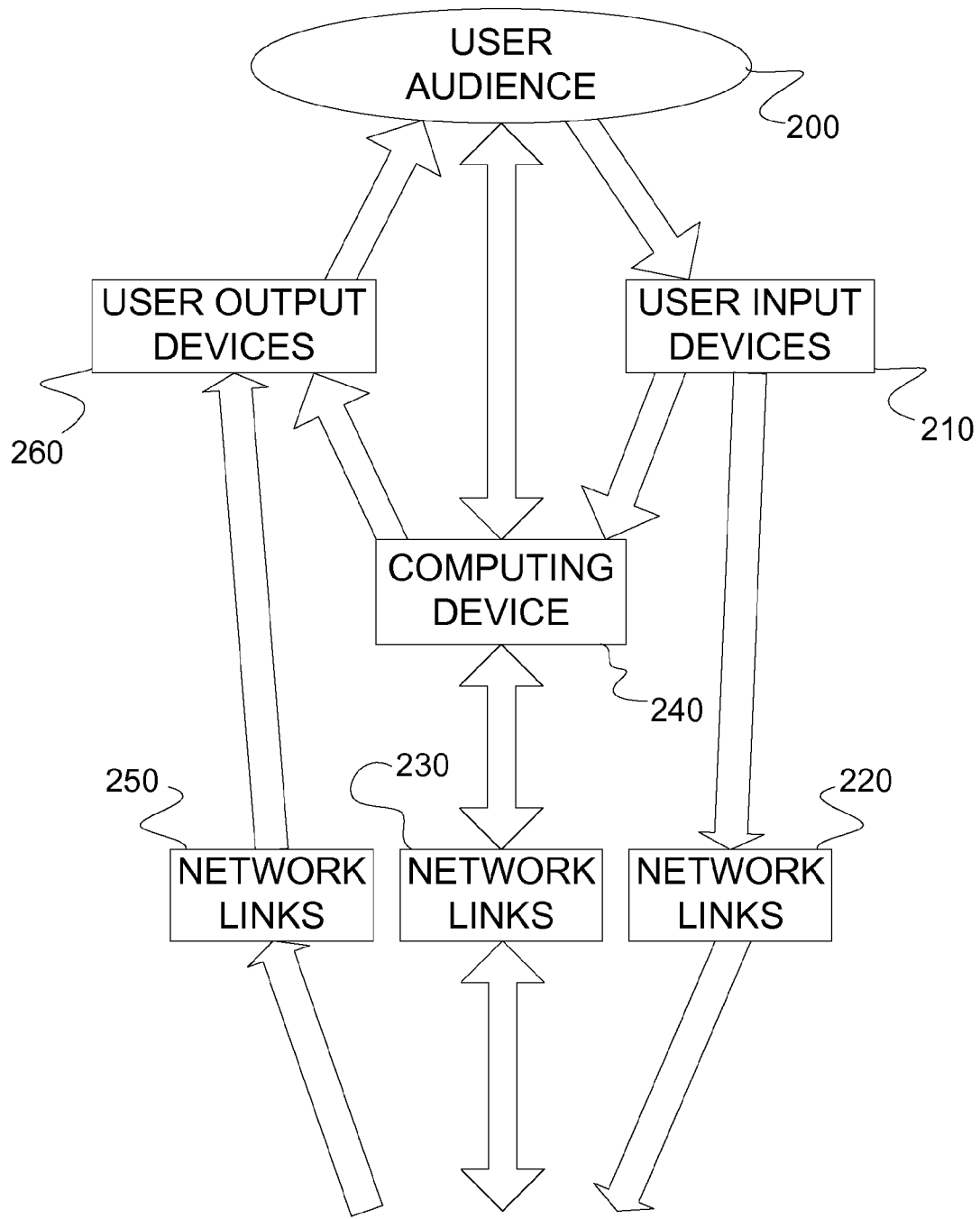
FIG. 2 shows an example embodiment of a user node.

To better understand the figures, reference numerals within the one hundred series (e.g., 100-199) are initially introduced in FIG. 1, reference numerals in the two hundred series (e.g., 200-299) are initially introduced in FIG. 2, reference numerals in the three hundred series (e.g., 300-399) are initially introduced in FIG. 3, and so on.

FIG. 1 shows a high-level view of an example distributed operant conditioning system, comprising a user node 100 in communication with several example subject nodes. Example subject nodes 150, 151, 152 and 153 are shown in the figure.

Figure 1A:
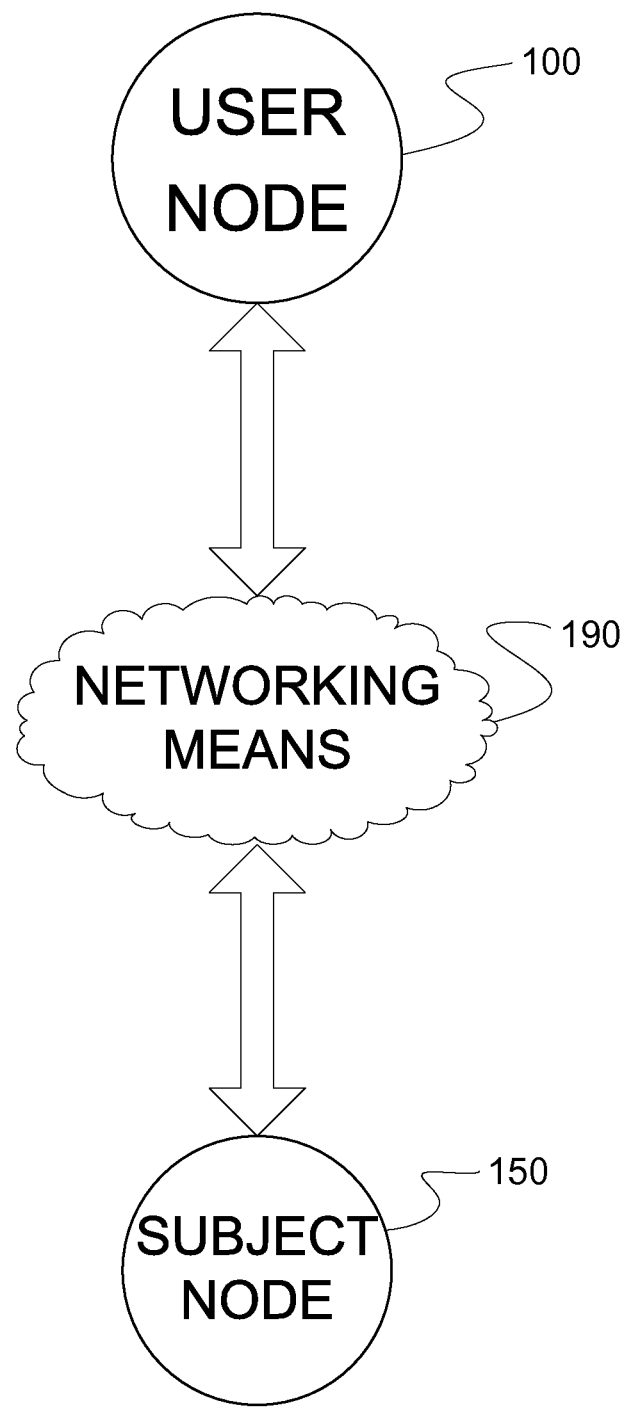
FIG. 1A shows the user node in communication with a single example subject node using networking means.

FIG. 1A shows the user node 100 in communication with the example single subject node 150 using networking means 190.

FIG. 2 shows a high-level view of an example embodiment of the user node 100. Depicted at the user node are the user audience 200, computing device 240 operatively connected to network links 230, user input devices 210 operatively connected to network links 220, and user output devices 260 operatively connected to network links 250.

Computing device 240 can be a general purpose computer comprising:
(a) processing means such as one or more CPUs (Central Processing Units),
(b) one or more input devices,
(c) one or more output devices,
(d) addressable memory, and
(e) mass storage for storing large amounts of data, such as programs.

The programs to be stored and operable in computing device 240 include an operating system, including drivers for both the integrated user input devices and the external user input devices 210, drivers for both the integrated user output devices and the external user output devices 260, and a web browser.

Special purpose programs stored and operable in computing device 240 will be described in the context of the additional embodiments shown later. In the specification and drawings, when so equipped, the computing device as particularized in the context of an example embodiment may be denoted with a descriptive suffix as an aid (i.e., computing device 240VIP when equipped with programming for use as a Voice over Internet Protocol device, computing device 240ZB when equipped with programming for use as a ZigBee control device, and so on.)

As will also be shown in additional example embodiments, the computing device can have any form factor: for example, that of a desktop computer, a portable computer such as a laptop, netbook, notebook, tablet computer, or the like, a personal digital assistant ("PDA") equipped with a web browser, or a 3G, 4G (or higher) cellular device similarly equipped and internet-enabled.

In the various more particularized example embodiments to follow, any of the network links 220, 230, and/or 250 may be an internal part of an explicitly illustrated device (i.e., an internal network card in a computing device, an internal interface circuit in a telephone device, etc.).

Depending on the form factor, one or more input devices such as a keyboard, trackball, touchpad, mouse, stylus pen, mouse, joystick or the like can be integrated with computing device 240 and/or be external, i.e., one or more of the input devices 210. Similarly, display devices can be integrated with the computing device 240 and/or be external, i.e., one or more of the output devices 260.

As used in this description and in the appended claims, "user audience" means one or more people assembled at the user node as a group, classroom or other audience. The user audience can include a moderator for the group, such as a teacher for a class in an educational setting or presenter in an entertainment setting. In a behavior modification setting, the user audience may consist of one person, such as therapist, psychologist or the like. In the figures to follow, where the user audience 200 is illustrated as a single figure it is understood that an associated group, if applicable, is implicitly understood even if not explicitly shown.

Figure 2A:
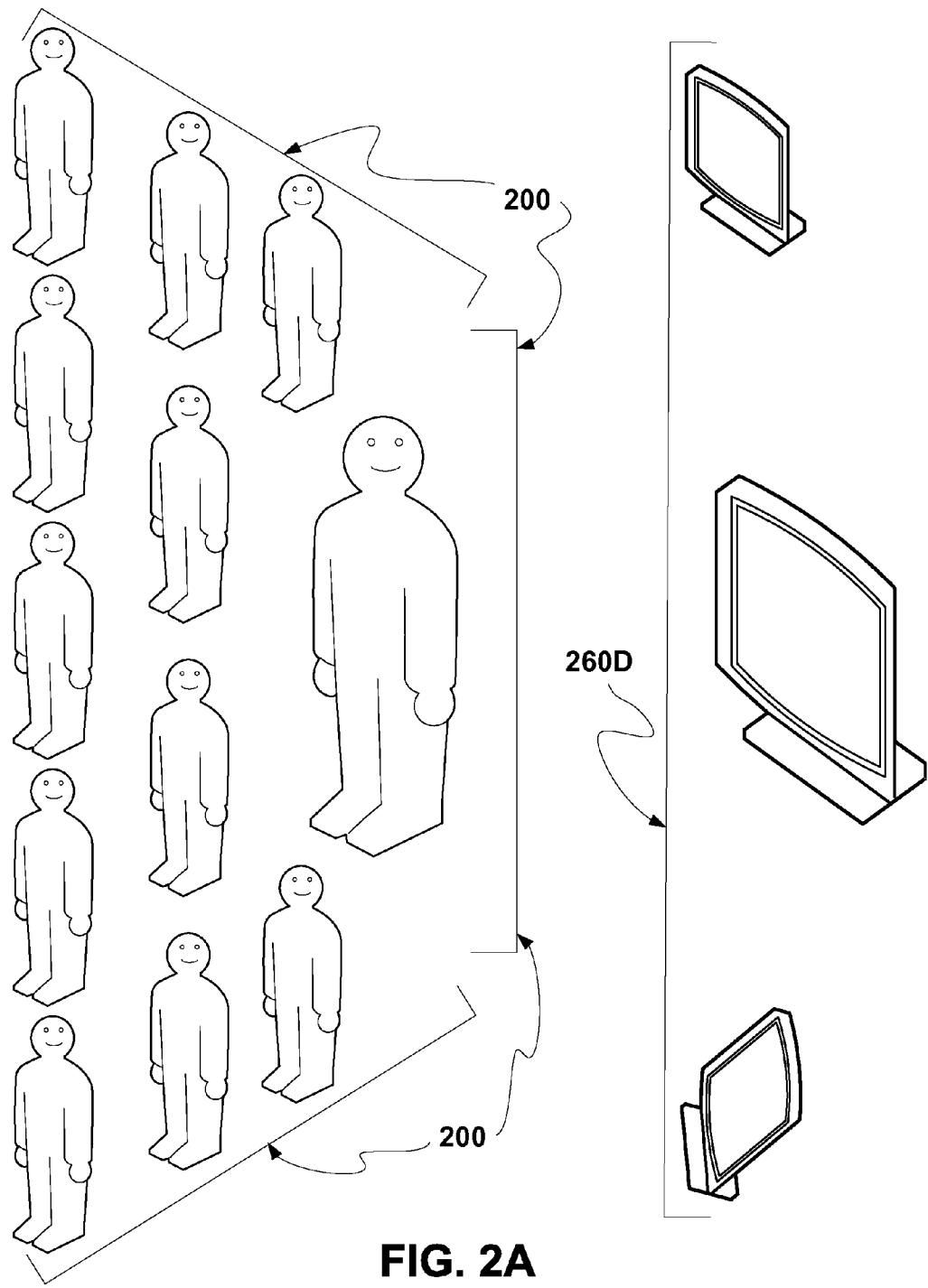
FIG. 2A illustrates an example of a user audience at the user node with the display means.

Referring to FIG. 2A, illustrated is the user audience 200 with a display means 260D shown as a plurality of display monitors or screens suitably sized and/or oriented for the user audience.

Figure 3A:
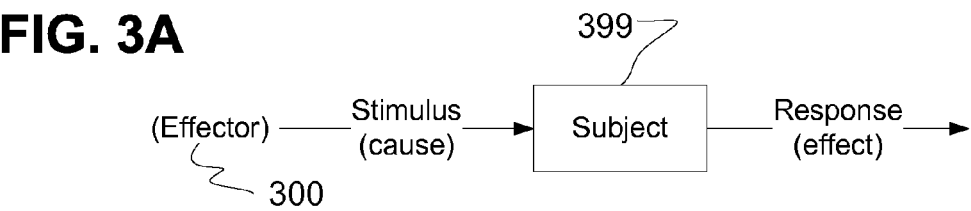
FIGS. 3A, 3B, 3C & 3D illustrate a fundamental paradigm and principles for use of the embodiments.

Referring to FIGS. 3A, 3B, 3C, & 3D, a fundamental paradigm and principles for use of the embodiments will be described. FIG. 3A shows as a baseline a model used in classical conditioning: An Effector 300 provides (in other words effects, or effectuates) a stimulus to a Subject 399 and the Subject then gives a response. In other words, the Stimulus (or cause) causes the Response (or effect), which was initiated by the Effector.

Figure 3B:
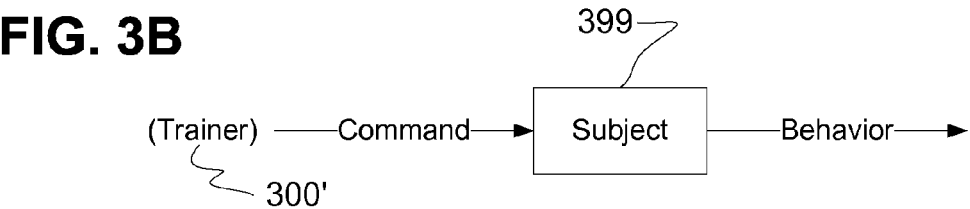

FIG. 3B shows the case where the Effector is, by way of example, a Trainer (or teacher) 300' giving a command to a subject animal (or subject child) 399' so that the Subject then gives a behavior in response (for example, sitting in response to the command "SIT", or silencing in response to "HUSH"). The subject has responded to the command, which was initiated by the Trainer (or teacher).

Figure 3C:
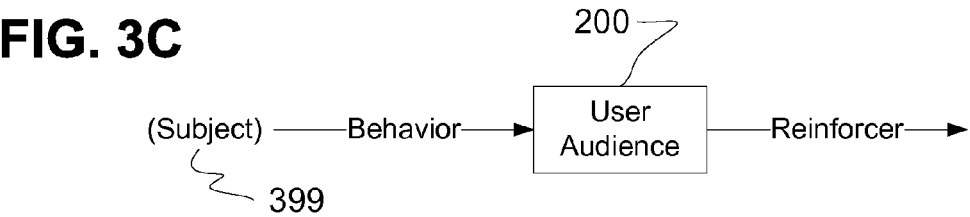

FIG. 3C depicts an operant conditioning scenario wherein the subject 399 voluntarily, or operantly, offers a behavior to a User Audience 200. The User Audience, as shown in the embodiments herein, responds to the observation of a desired or selected behavior by providing a conditioned reinforcer. The Subject has operated on the environment to cause it to be reinforced. In the example case of a subject animal, the animal is training the trainer to give it treats, or in the example case of a subject child, the child is training the teacher to give her treats, or allow play with a toy, etc.

Figure 3D:
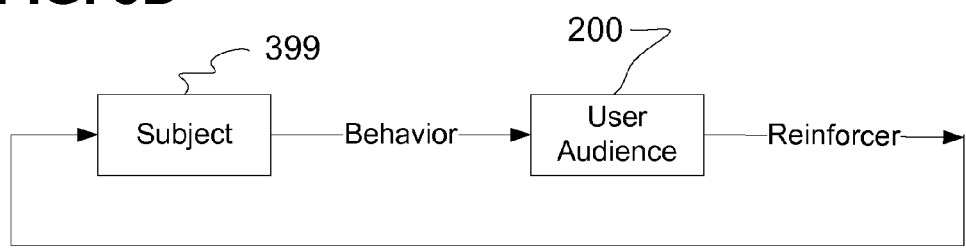

FIG. 3D illustrates the fact that the reinforcer is given to the Subject by the User audience, thereby closing the loop and illustrating the interactive nature inherent in the underlying principles of operant conditioning and their use in the embodiments: with reference to the baseline model of FIG. 3A the Subject is acting as an effector to the User Audience while the User Audience is acting as an effector to the Subject. In other words, both the User audience and the Subject are each simultaneously acting as a subject to the other.

This interactivity is highly educational and entertaining in that, similar to improvisational forms of comedy, the results are inherently surprising and unexpected.

Figure 4:
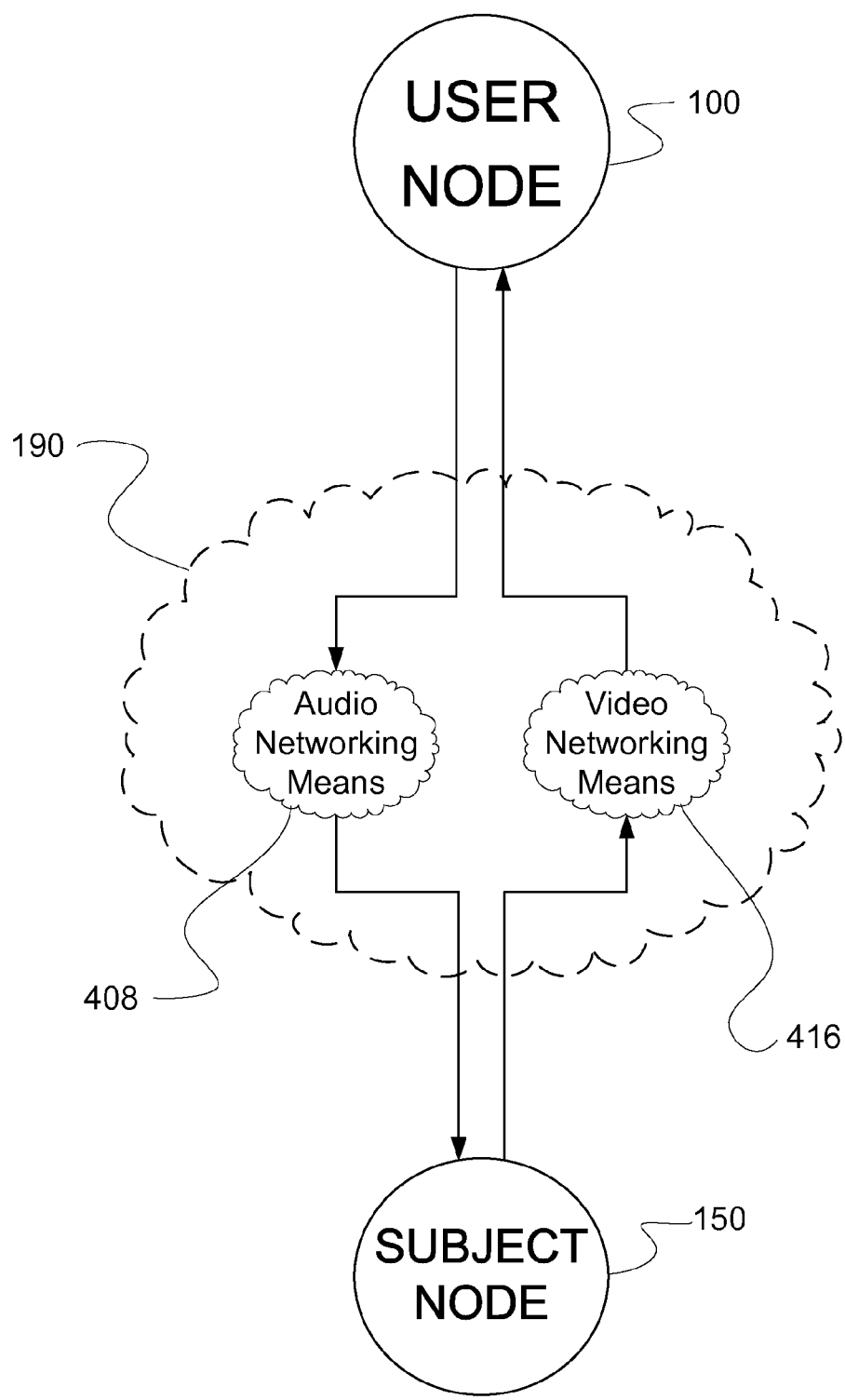
FIG. 4 shows a high-level view of an example embodiment of a user node and a subject node with audio networking means and video networking means between nodes.

Referring to FIG. 4, shown is a high-level view of an example embodiment of User node 100 and an example Subject node 150. The Networking means 190 of previous high-level diagram of FIG. 1A is illustrated as having two example components, audio networking means 408 and video networking means 416.

Referring to FIG. 4A, a finer level of detail is shown. Illustrated is an example subject 399 at the example subject node; in this figure the example subject is illustrated as a child.

User node output Network link 431 operatively connects with or to the audio networking means 408, User node input Network link 432 operatively connects with or to the video networking means 416, Subject node output Network link 433 operatively connects with or to the video networking means 416, and Subject node input Network link 434 operatively connects with or to the audio networking means 408.

In the more particularized example embodiments to follow, any of the network links may be internal components of an explicitly illustrated device (i.e., an internal interface circuit in a telephone device, an internal network card with drivers in a computing device, internal sound or display card with drivers in a computing device, etc.).

At the user node the user audience 200 observes the subject on display means 260D through video camera means 414 located at the subject node. The display means 260D can be a plurality of display monitors or screens suitably sized and/or oriented for the user audience, as previously described with reference to FIG. 2A. Display means 260D can be one or more of the user output devices 260 of FIG. 2.

If at the subject node the subject is an animal in an enclosure with obstructions, or in a particularly large enclosure or habitat such as in an animal park or zoo with a natural habitat, then the video camera means 414 at the subject node can be a networked suitable plurality of cameras such that the subject animal is not obscured, as will be shown in later embodiments.

Referring again to FIG. 4A, the signal from the video camera means 414 is! transmitted through video networking means 416. The user audience at the user node communicates to the subject by emitting suitably audible sound signals 402 which are picked up by a microphone device 404. These sound signals are transmitted through audio networking means 408 to a suitably amplified speaker means 410 in a proximity to the subject at the subject node such that it perceives the emitted sounds 402'. The speaker means can be a suitably located plurality of suitably amplified speaker devices if needed, as will be shown in later embodiments.

The emitted sounds can be verbalizations such as "Good boy/girl!" or "Yes!" These are conditioned reinforcers, and when precisely timed serve as marker signals to the subject. More precisely in serving as a distinctive marker signal to the subject, the user audience can directly make a unique sound (e.g., a clucking sound, or the sound of a hand clap). Most precisely the user audience can use a device such as a metallic party clicker (a handheld device with a bendable noise producing flap), a whistle, horn or the like, operated in proximity to microphone device 404.

The emitted sounds can also be signals serving as cues, for example verbalizations such as "HUSH" or "TOUCH". The user audience can therefore generate both marker signals and cues, independently as needed, suitable for the example subject at hand and the session at hand, for use with the example embodiment operations described later, such as shaping a behavior (FIG. 11), bringing a behavior under cue control (FIG. 12), or shaping and/or demonstrating behavior chains (FIG. 13).

Although in the present example the conditioned reinforcer serving as a marker signal is auditory, in accordance with the underlying principles of the embodiments, this conditioned reinforcer can be a stimulus from any sensory mode (e.g., light, sound, smell, tactile, etc.). For species with electroreception for example, such as some fish, sharks and rays, the stimulus may be an electric field. As another example, for many species of fish a flash of light may be more appropriate than a noise. An IR (Infra-red) light source such as an IR LED (light Emitting Diode), may be appropriate for some snakes. For species of animals that are tetrachromats, such as some birds, bees or dragonflies, for example, an UV (Ultra-violet) light source such as an UV LED may be appropriate.

For the present example, in the description of an audible marker signal serving as the conditioned reinforcer signal the microphone device 404 and audio networking means 408 of FIG. 4A can be embodied by a telephone operating over the PSTN (Public Switched Telephone Network) such as telephone 400A and PSTN network 408PN as shown in FIG. 4B. The subject node input network link is shown particularized as 434PN, which can be embodied by a telephone and/or speaker phone device with speaker means 410 either operatively connected to or a component of the device.

FIG. 4C shows, equivalent in function, a VoIP (Voice over Internet Protocol) phone 400B operating over an IP network (i.e., the internet network) 408IP. The subject node input network link is shown particularized as 434IP, which can be embodied by a VoIP telephone similar to that at the user node (400B).

FIG. 4D illustrates as a functionally equivalent example the use of a computing device 240VIP which can be the equivalent of computing device 240 of FIG. 2 where one of the user input devices is a microphone (either integrated or one of the external user input devices 210 in FIG. 2). This equivalent functionality is enabled when the computing device programming comprises an operating system including drivers for a microphone device, a sound card, web browser, and software for VoIP service (also known as "softphone" software). The subject node input network link is again shown particularized as 434IP, which can be embodied by either a telephone similar to VoIP telephone 400B of the previous example or a VoIP softphone similar to 240VIP at the user node.

The marker signal, instead of a clicker or whistle, for example, can also be any of the distinctive tones produced by a DTMF telephone digit key. The user audience, once connected over the network to the subject node, can generate one (or more) of these tones recognizable to the subject as a conditioned reinforcer.

As with the emitted signals previously discussed, some of the tones can also serve as cues, and so the user audience can therefore generate both marker signals and cues, independently as needed, suitable for the example subject at hand and the session at hand, for use with the example operations described later, such as shaping a behavior (FIG. 11), bringing a behavior under cue control (FIG. 12), or shaping and/or demonstrating behavior chains (FIG. 13).

These and substantially equivalent example embodiments such as the use of a cellular phone instead of a landline and an analog phone with the use of a VoIP analog telephone adaptor (ATA) will be shown and described further in the context of other additional embodiments and their variants presented later.

Referring to FIG. 4E, the camera means 414 and video networking means 416 of FIG. 4A can be embodied by an IP (Internet Protocol) camera 414IP (also referred to as a network camera) or functional equivalent connected to the internet network 416IP with the user audience employing a suitably equipped web-enabled computing device 240IP which can be the equivalent of computing device 240 of FIG. 2 (shown here with an integrated display) with an operating system including display drivers and web browser.

An external display monitor or plurality of display monitors suitably oriented for the user audience, operably connected to the computer, such as one of the external user output devices 260 in FIG. 2 would embody the same functionality as the integrated display illustrated. The subject node output network link is shown particularized as 433IP. This network link, illustrated to functionally show the flow of image data information, could be integrated in hardware and/or software with the prior network link illustrated to functionally show the flow of audio signal information. This would be the case, for example, in the context of the integrated audio-visual content of a webcast, as will be shown in the context of later additional embodiments.

As discussed earlier, if the subject is an animal in a large enclosure or habitat, the video camera means can be a networked suitable plurality of cameras such that the animal is not obscured. In the present case of an IP or network camera 414IP, this can be enabled by the use of commercially available multiple IP camera surveillance systems typically used in security applications. These network cameras as commercially available often have embedded Pan, Tilt and Zoom ("PTZ") functionality to aid in observing the subject animal as it moves.

Alternatively, instead of the IP network camera, a suitably equipped 3G, 4G or higher cellular phone 414C, PDA (Personal Digital Assistant), smart phone or the like with an integrated video camera, web browser and web conferencing application, either installed or hosted or both, can be used as shown in FIG. 4F to broadcast, webcast or otherwise stream video (and audio) from the subject node. Similarly, later figures will show examples of the use of such suitably equipped cellular phone or mobile personal appliance devices to both broadcast and display images of the subject for the user audience.

As will also be seen in various embodiments shown and described further later, the audio networking means 408 and visual networking means 416 of FIG. 4A can utilize the same or separate networks (e.g., telephone and/or internet networks) or be physically and/or logically integrated in hardware, software and/or firmware as implemented by multimedia computers equipped with webcams, videophones (also referred to as video telephones), or smart camera phones or the like. Commercially available video conferencing systems can also fill this functionality. Several such integrated embodiments, for example, are also represented in FIGS. 6A-6D. These integrated embodiments will be described further in the descriptions of later figures.

Figure 5:
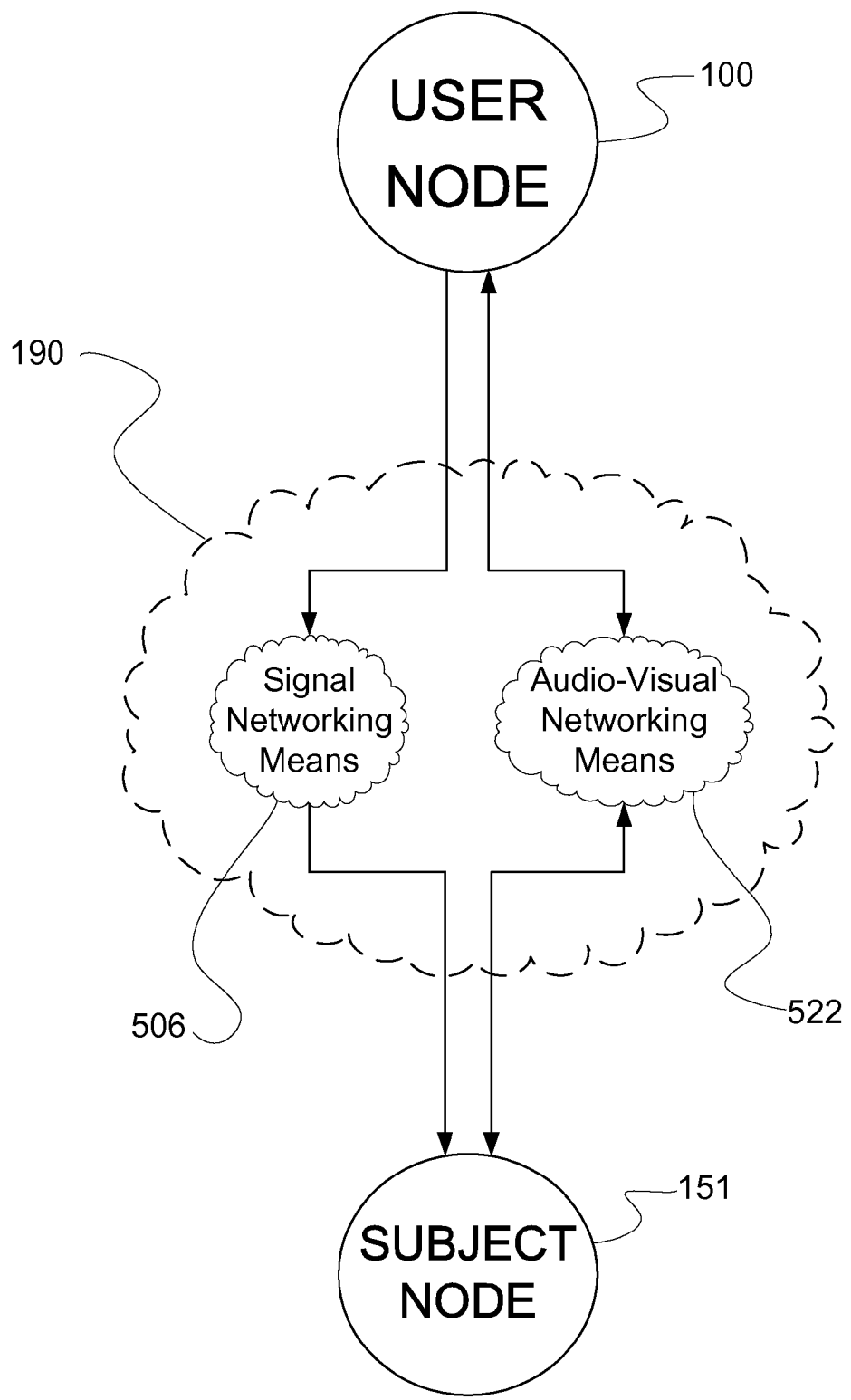
FIG. 5 shows a high-level view of an example embodiment of a user node and a subject node with signal networking means and audio-visual networking means between nodes.

Referring to FIG. 5, shown is a high-level view of an example embodiment of User node 100 and an example Subject node 151. The Networking means 190 of previous high-level diagram of FIG. 1A is illustrated as having two example components, signal networking means 506 and audio-visual networking means 522.

Figure 5A:
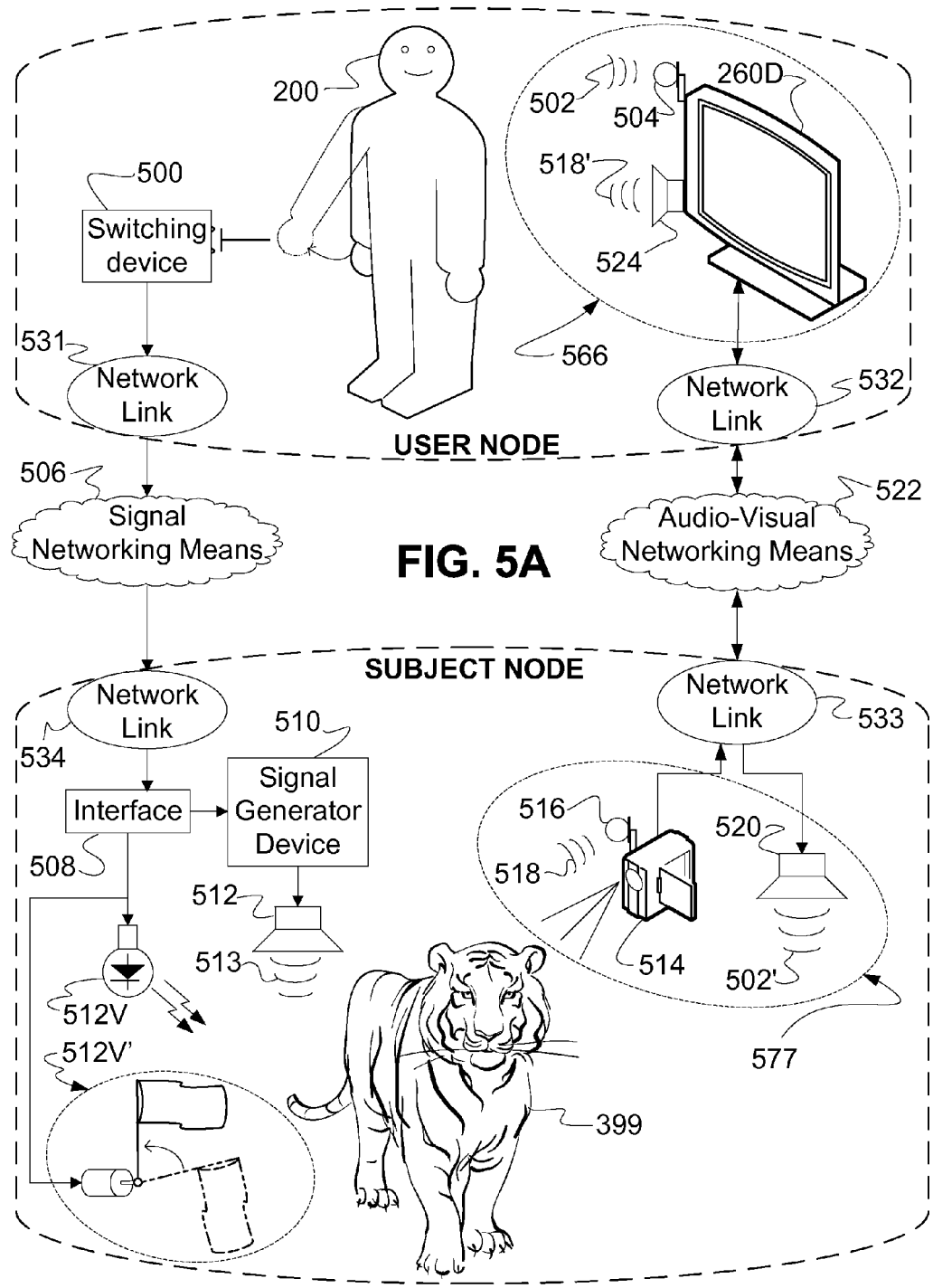
FIG. 5A shows finer detail of the example embodiment.

Referring to FIG. 5A, a finer level of detail is shown. Illustrated is an example subject 399 at the example subject node; in this figure the example subject is illustrated as a tiger, an exotic feline.

User node output Network link 531 operatively connects with or to the signal networking means 506, User node network link 532 operatively connects with or to the audio-visual networking means 522, Subject node network link 533 operatively connects with or to the audio-visual networking means 522, and input Subject node network link 534 operatively connects with or to the signal networking means 506. User node network link 532 in this example embodiment combines the functionality of a user node input link and user node output link, and similarly subject node network link 533 combines the functionality of a subject node input link and a subject node output link.

In the more particularized example embodiments to follow, any of the network links illustrated to show functionality may be integrated in hardware and/or software or be internal components of another explicitly illustrated device (i.e., an internal interface circuit in a telephone device, an internal network card with drivers in a computing device, internal sound or display card with drivers in a computing device, etc.). Where not explicitly shown, the input and/or output network links are implicit in the configuration: i.e., a network link configured to interconnect with the PSTN network could be embodied by an "RJ-11" (telephone) jack (but not illustrated), whereas a network link configured to interconnect with the internet (IP) network could be embodied by an "RJ-45" (8P8C or Ethernet) jack (but not illustrated).

At the user node the user audience 200 observes the subject on display means 260D through video camera means 514 located at the subject node. The image data is transmitted through audio-visual networking means 522. The display means 260D can be a plurality of display monitors or screens suitably sized and/or oriented for the user audience, as previously described with reference to FIG. 2A. Display means 260D can be one or more of the user output devices 260 of FIG. 2.

Referring again to FIG. 5A, the user audience communicates to the animal by emitting suitably audible sounds 502 directed towards microphone device 504. These sounds are transmitted through the audio-visual networking means 522 to a suitably amplified speaker means 520 in proximity to the subject such that the subject perceives the emitted sounds 502'. The speaker means can be a suitably located plurality of speaker devices if needed, as will be shown in later embodiments. The emitted sounds can serve as either marker signals or cues, independently as needed, suitable for the example subject at hand and the session at hand, for use with the example embodiment operations described later.

A person (not shown) located at the subject node can optionally communicate verbalized information or instructions 518 to the user audience by speaking into microphone device 516. These verbalizations are transmitted through the audio-visual networking means 522 to a suitably amplified speaker means 524 at the user node so that the user audience hears the emitted verbalizations 518'.

The user audience can activate a switching device 500 which then transmits a switched signal responsive to this switching device through signal networking means 506 to the subject node. Through interface 508, a suitable relay device as shown later, this switched signal energizes signal generator device 510 to produce a predefined sound serving as a marker signal such as an audio tone, whistle, horn, chirp or the like. Although described here as generating a single tone, whistle, horn, chirp, or the like, the signal generator device 510 can be a switched plurality of tone (or waveform) generating circuits or similarly a selectably tunable waveform or tone generator. The generated signals can also serve as cues, suitable for the example subject at hand and the session at hand, for use with the example operations described later. The audible signals are emitted by suitably amplified speaker means 512 in proximity to the subject such that the subject perceives the emitted sounds 513.

As discussed previously, the conditioned reinforcer signal (or a cue signal) to the subject can be a stimulus from any sensory mode (e.g., light, sound, smell, tactile, electro-reception, etc.).

In addition to an acoustic transducer (as exemplified by speaker means 512), another example of effectuating a marker signal (or a cue signal) is illustrated as visual signal source 512V which is energized by interface 508. As discussed earlier, a flash of light may be an appropriate conditioned reinforcer signal when the subject is a fish, an IR light source such as an IR LED may be more appropriate for some snakes as subjects, and an UV light source such as an UV LED may be more appropriate when the subject is a tetrachromatic animal such as with some birds, bees or dragonflies.

Another example of a visual marker signal (or cue signal) would be the actuatable raising of a flag or sign or the like, as illustrated by the alternate example of assembly 512V' depicting an actuator motor raising a flag in such a way as to be visible to the subject. As with acoustic signals, the generated visual signals can serve not only as marker signals, but also serve as cues to the subject.

Additional example embodiments are now described in further detail for the generation of marker signals (or cue signals) by the user audience using a switching device at the user node, with the relevant networking means, interfacing, and signal generating means whereby the signal is communicated to the subject at the subject node.

Referring to FIG. 5B, a DTMF (Dual Tone Multi Frequency or "Touch-Tone", also known as tone-dialing) telephone 500A is used by the user audience as a switching device at the user node. The telephone communicates over a PSTN (Public Switched Telephone Network) 506PN to the subject node. The call is received at the subject node by DTMF Relay 508A. The relay is energized when the user audience enters preprogrammed digits on the telephone. A signal generator device 510A, activated by the DTMF relay, generates an audio marker signal (or cue signal). This signal generator device can be any distinctive noise producing device such as a buzzer, chime, horn, whistle, etc.

Although described here as generating a single tone, whistle, chirp, or the like, the signal generator device 510A can be a switched plurality of tone (or waveform) generating circuits or similarly a selectably tunable waveform or tone generator. A suitably amplified speaker means 512 is located in proximity to the subject such that the emitted sound 513 is readily perceived by it as a known marker signal (or cue signal). In addition to an acoustic transducer, the example effectuation of a visual signal is illustrated as example visual signal source 512V which is energized by DTMF Relay 508A. As with acoustic signals, the generated visual signals can serve not only as marker signals, but also serve as cues to the subject.

Referring to FIG. 5C, instead of the DTMF telephone 500A in FIG. 5B a DTMF capable cellular phone as shown by 500A' is used instead by the user audience at the user node as a switching device. The telephone communicates over the PSTN (Public Switched Telephone Network) 506PN to the subject node as previously described such that the emitted sound 513 is readily perceived by the subject as a known marker signal (or cue signal). In addition to an acoustic transducer, the example effectuation of a visual signal is again illustrated as example visual signal source 512V which is energized by DTMF Relay 508A. As with acoustic signals, the generated visual signals can serve not only as marker/reinforcer signals, but also serve as cues to the subject.

Referring to FIG. 5D, computing device 240W is used as a switching device. The computing device 240W can be the equivalent of computing device 240 of FIG. 2 (shown here with an integrated display) with an operating system, input device drivers, web browser, and programs including application software compatible with Web Relay 5081P. This software is commercially available either installed or commercially hosted or both. This programming enables the computing device 240 to function as a switching device wherein the user audience uses a mouse, keyboard or other user input device (either one of the integrated input devices or one of the external user input devices 210). The computing device 240W, when so used, acts as a switching device to communicate over the IP (Internet Protocol) Network 5061P to the subject node. At the subject node a Web Relay 5081P containing an embedded web server is energized in response to the pre-programmed inputs provided by the user audience. A signal generator device 510B, powered by the relay, generates an audio signal. This signal generator device can be any distinctive noise producing device such as a buzzer, chime, horn, whistle, etc. A suitably amplified speaker means 512 is located in proximity to the subject such that the emitted sound 513 is readily perceived by the subject. In addition to an acoustic transducer, the example effectuation of a visual signal is again illustrated as example visual signal source 512V which is energized by Web Relay 5081P. As with acoustic signals, the generated visual signals can serve not only as marker signals, but also serve as cues to the subject.

Referring to FIG. 5E, a suitably equipped (e.g., internet enabled) cellular phone device 240W', PDA or the like is used by the user audience at the user node as a switching device. This internet enabled computing device can be equipped with application software compatible with Web Relay 5081P. This software is commercially available either installed or commercially hosted or both. This programming enables the computing device 240W' to function as a switching device wherein the user audience uses a keypad, pen stylus, touch screen or other user input to communicate over the IP Network 5061P to the subject node. At the subject node the Web Relay 5081P containing an embedded web server is energized in response to the pre-programmed inputs provided by the user audience as previously described such that the emitted sound 513 is readily perceived by the subject. In addition to an acoustic transducer, the example effectuation of a visual signal is again illustrated as example visual signal source 512V which is energized by Web Relay 5081P. As with acoustic signals, the generated visual signals can serve not only as marker signals, but also serve as cues to the subject.

If the subject node does not have internet access throughout, such as might be the case where at the subject node the subject is an animal in a particularly large enclosure or habitat such as in an animal park or zoo with a natural habitat, then the following additional embodiments can be used. (As noted earlier, the video camera means at the subject node can be a networked suitable plurality of cameras such that the subject animal is not obscured, as will be shown in later embodiments).

Referring to FIG. 5F, the internet enabled computing device 240HA can be the equivalent of computing device 240 of FIG. 2 (shown here with an integrated display) with an operating system, input device drivers, web browser, and programs including application software compatible with HA ("Home Automation") Gateway 507HA. This software is commercially available either installed or commercially hosted or both. This programming enables the computing device 240 to function as a switching device wherein the user audience uses a mouse, keyboard or other user input device (either one of the integrated or one of the external user input devices 210). The computing device 240HA, when so used, acts as a switching device to communicate over the IP Network 5061P to the subject node. At the subject node, responsive to the switched signal from the user node using the Home Automation application software, the Internet to HA Gateway 507HA energizes the HA Power Line Transceiver 508HA. If the home automation software program, gateway, and transceiver used are X-10 based, for example, then the transceiver is activated by the X-10 commands sent through the power line wiring (extension cords can be used at the subject node). If the home automation application software, gateway, and transceiver used are INSTEON based, for example, then the transceiver is activated by the INSTEON commands sent through the power line wiring and the additional wireless signal inherent in the protocol. When the HA Power Line Transceiver 508HA is energized, the signal generator device 510B, powered by the relay of the transceiver, generates an audio signal as previously described such that a suitably amplified speaker means 512 is located in proximity to the subject such that the emitted sound 513 is readily perceived by the subject as a known marker signal (or cue signal). The speaker means can be a suitably located plurality of suitably amplified speaker devices if needed, as will be shown in later embodiments. In addition to an acoustic transducer, the example effectuation of a visual signal is again illustrated as example visual signal source 512V which is energized by HA Power Line Transceiver 508HA. As with acoustic signals, the generated visual signals can serve not only as marker signals, but also serve as cues to the subject.

Referring to FIG. 5G, use of an example wireless protocol at the subject node will be described. The internet enabled computing device 240ZW can be the equivalent of computing device 240 of FIG. 2 (shown here with an integrated display) with an operating system, input device drivers, web browser, and programs including application software compatible with Internet to Z-Wave Gateway 507ZW. This software is commercially available either installed or commercially hosted or both. This programming enables the computing device 240 to function as a switching device wherein the user audience uses a mouse, keyboard or other user input device (either one of the integrated or one of the external user input devices 210). The computing device 240ZW, when so used, acts as a switching device to communicate over the IP Network 5061P to the subject node. At the subject node, responsive to the switched signal from the user node using the Z-Wave software program, the Internet to Z-Wave Gateway 507ZW energizes the Z-Wave Appliance Module 508ZW. When energized, the signal generator device 510B, powered by the relay of the Z-Wave Appliance Module, generates an audio signal as previously described such that a suitably amplified speaker means 512 is located in proximity to the subject such that the emitted sound 513 is readily perceived by the subject as a known marker signal (or cue signal). The speaker means can be a suitably located plurality of suitably amplified speaker devices if needed, as will be shown in later embodiments. In addition to an acoustic transducer, the example effectuation of a visual signal is again illustrated as example visual signal source 512V which is energized by Z-Wave Appliance Module 508ZW. As with acoustic signals, the generated visual signals can serve not only as marker signals, but also serve as cues to the subject.

Referring to FIG. 5H, another example of the use of a wireless protocol at the subject node will be described. If the subject node does not have internet access throughout, such as might be the case where at the subject node the subject is an animal in a particularly large enclosure or habitat such as in an animal park or zoo with a natural habitat, but there is internet access in nearby administrative buildings, the following example embodiment can be used.

The wireless example illustrated herein is the ZigBee suite of protocols (based on the IEEE 802.15.4 standard) but any radio specification for wireless personal area networks (WPAN's) would enable the example embodiment with the same functionality in substantially the same way to achieve the same result. The internet enabled computing device 240ZB shown in the figure can be the equivalent of computing device 240 of FIG. 2 (shown here with an integrated display) with an operating system, input device drivers, web browser, and programs including application software compatible with ZigBee Modem 507ZB. This software is available either installed or commercially hosted or both. This programming enables the computing device 240ZB to function as a switching device wherein the user audience uses a mouse, keyboard or other user input device (either one of the integrated or one of the external user input devices 210). The computing device 240ZB, when so used, acts as a switching device to communicate over the IP Network 5061P to the subject node. At the subject node, for example in an administrative building with internet access, an internet enabled general purpose computer 240USB with USB (Universal Serial Bus) ports and drivers is operatively connected to the internet, with a web browser and programs including application software compatible with ZigBee USB Modem 507ZB. Responsive to the switched signal from the user node using the application software, the computer 240USB sends a command to USB ZigBee Modem 507ZB, which wirelessly energizes the ZigBee Relay 508ZB, closing its contacts. The signal generator device 510B, powered by the ZigBee relay, generates an audio signal as previously described such that suitably amplified speaker means 512 is located in proximity to the subject and the emitted sound 513 is readily perceived by it as a known signal. The speaker means can be a suitably located plurality of suitably amplified speaker devices if needed, as will be shown in later embodiments. In addition to an acoustic transducer, the example effectuation of a visual signal is again illustrated as example visual signal source 512V which is energized by ZigBee Relay 508ZB. As with acoustic signals, the generated visual signals can serve not only as marker signals, but also serve as cues to the subject.

Referring to FIG. 5I, another example of the use of a wireless protocol at the subject node will be described where the subject node may not have internet access throughout but there is internet access in nearby administrative buildings. The internet enabled computing device 240BT can be the equivalent of computing device 240 of FIG. 2 (shown here with an integrated display) with an operating system, input device drivers, web browser, and programs including application software compatible with Bluetooth Relay 508BT. This programming enables the computing device 240BT to function as a switching device wherein the user audience uses a mouse, keyboard or other user input device (either one of the integrated or one of the external user input devices 210). The computing device 240BT, when so used, acts as a switching device to communicate over the IP Network 5061P to the subject node. At the subject node, for example in an administrative building with internet access, an internet enabled general purpose computer 507BT with Bluetooth capability is operatively connected to the internet, with a web browser and programs including application software compatible with Bluetooth Relay 508BT. Responsive to the switched signal from the user node using the Bluetooth relay compatible application software, the computer 507BT wirelessly energizes the Bluetooth Relay 508BT. When energized, the signal generator device 510B, powered by the Bluetooth relay, generates an audio signal as previously described such that suitably amplified speaker means 512 is located in proximity to the subject and the emitted sound 513 is readily perceived by the subject. The speaker means can be a suitably located plurality of suitably amplified speaker devices if needed, as will be shown in later embodiments. In addition to an acoustic transducer, the example effectuation of a visual signal is again illustrated as example visual signal source 512V which is energized by Bluetooth Relay 508BT. As with acoustic signals, the generated visual signals can serve not only as marker signals, but also serve as cues to the subject.

FIG. 5J shows an example embodiment for use with the internet. A DTMF telephone 500A is used by the user audience at the user node as a switching device. The telephone is connected to an IP (Internet Protocol) network 5061P by a VoIP (Voice over Internet Protocol) adaptor 502, also known as a VoIP ATA (Analog Telephone Adaptor). At the subject node another VoIP ATA 502' connected to the internet network provides a telephone connection for DTMF relay 508A which as described previously is energized in response to the preprogrammed digits entered by the user audience. A signal generator device 510A, powered by the relay, generates an audio signal. The signal generator device can be any distinctive noise producing device such as a buzzer, chime, horn, etc. Although described here as generating a single tone, whistle, chirp or the like, the signal generator device 510A can be a switched plurality of tone (or waveform) generating circuits or similarly a selectably tunable waveform or tone generator. A suitably amplified speaker means 512 is located in proximity to the subject such that the emitted sounds 513 are readily perceived by the subject as known marker signals (or cue signals). In addition to an acoustic transducer, the example effectuation of a visual marker signal is again illustrated as example visual signal source 512V which is energized by DTMF relay 508A. As with acoustic signals, the generated visual signals can serve not only as marker signals, but also serve as cues to the subject.

Referring to FIG. 5K, a dedicated VoIP telephone 500V is used by the user audience at the user node as a switching device instead of the DTMF telephone 500A and VoIP ATA adaptor 502 of FIG. 5J. The telephone is connected directly to the IP (Internet Protocol) network 5061P. The user audience communicates over the internet network to the subject node as previously described such that the emitted sounds 513 are readily perceived by the subject as known marker signals (or cue signals). In addition to an acoustic transducer, the example effectuation of a visual signal is again illustrated as example visual signal source 512V which is energized by DTMF relay 508A. As with acoustic signals, the generated visual signals can also serve not only as marker signals, but also serve as cues to the subject.

Additional embodiments are shown in FIGS. 6A, 6B, 6C & 6D. These embodiments enable the audio-visual networking means 522 previously described in FIGS. 5 & 5A.

Referring to FIG. 6A, at the user node a suitably equipped (e.g., internet enabled multimedia) computer 666 with display is used by the user audience. This suitably equipped computer has an integrated microphone device and speakers, and incorporates the components which were also shown in FIG. 5A by assembly 566. The internet enabled computing device 666 can be the equivalent of computing device 240 of FIG. 2 (shown here with an integrated display) with an operating system, input device drivers, web browser, and programs including web conferencing application software, either installed or commercially hosted or both. This computer communicates over an IP (Internet Protocol) Network (i.e., the internet) 5221P to the subject node. At the subject node, a CCTV (Closed-Circuit Television) camera 5141P that uses Internet Protocol to transmit image data is used. This camera is also known as an IP or network camera, typically used in security and home monitoring applications. The cameras are available with two-way audio capability and therefore such converged devices can embody both of the functionalities previously described and shown in FIGS. 4 & 4A as audio networking means 408 and video networking means 416, as well as the audio-visual networking means 522 previously described and shown in FIGS. 5 & 5A.

Referring to FIG. 6B, instead of the computer 666 at the user node, a similarly suitably equipped 3G, 4G or higher cellular phone, PDA, smart phone or the like with a web browser and web conferencing application, either installed or hosted or both, can be used as shown by 666'. This web-enabled cellular device communicates over the IP (Internet Protocol) Network 5221P to the subject node. At the subject node, the IP camera 5141P is used as previously described with respect to FIG. 6A.

Referring to FIG. 6C, instead of the IP network camera 5141P at the subject node, a suitably equipped 3G, 4G or higher cellular phone, PDA, smart phone or the like with an integrated video camera and audio capability, web browser and web conferencing application, either installed or hosted or both, can be used as shown by 666C' to broadcast, webcast or otherwise stream video (and audio) from the subject node.

Referring to FIG. 6D, at the user node a suitably equipped web-enabled cellular phone device 666' as previously described with respect to FIG. 6B communicates over the IP (Internet Protocol) Network 5221P to the subject node. The received audio-visual content is output to display means 260D. The connection can be made via a port such as HDMI ("High Definition Multimedia Interface"), DVI ("Digital Video Interface"), Firewire, USB, or the like. Display means 260D can be a plurality of suitably sized and/or oriented display monitors or screens for the user audience.

If the subject is an animal and at the subject node the subject animal is in an enclosure with obstructions, or a particularly large enclosure or habitat such as in an animal park or zoo with a large natural habitat, the video camera means can be a networked plurality of cameras suitable in number such that the subject animal is not obscured as it moves throughout its habitat. This functionality is enabled by commercially available IP network multiple camera surveillance systems. Often these cameras have PTZ (Pan, Tilt & Zoom) features embedded within the camera units. Even with this embedded PTZ capability, it would often be advantageous, and possibly necessary, to implement the video camera means as a plurality of cameras.

The additional embodiments shown herein will enable this functionality and features previously discussed for the example case of particularly vast animal enclosures, such as with animal parks and zoos emulating natural habitats, especially for animals such as zebra, giraffes, elephants and other such migratory animals. If nearby or on site administrative buildings have internet access, then the addition of one or more Wireless Access Points (WAPs) (possibly converged devices which also function as Routers and/or Ethernet switches or broadband modems) (and possibly directional antennas if needed) would allow for wireless internet access and therefore any of the previously shown embodiments using IP networking could be used, thus allowing animals in large enclosures or habitats such as in an animal park or zoo to be operantly conditioned in the same interactive manner as previously described, with the same educational and entertaining results. Any of the embodiments exemplified by FIGS. 4 & 4A (showing Audio Networking Means & Video Networking Means) or FIGS. 5 & 5A (showing Signal Networking Means & Audio-Visual Networking Means) wherein the networking means used between user and subject nodes used an IP network could thus be enabled. Commercially available web relays with embedded web servers as previously described are also available for wireless use (e.g., "Wi-Fi" relays). Therefore, the generation of marker signals (or cue signals) with the switched signal means described with reference to FIGS. 5, 5A, 5D, 5E, 5F, 5G, 5H, 5I, 5J, & 5K are enabled by such use of WAP's (in other words, the term "Web relay" as used in the specification and appended claims includes "Wi-Fi" relays).

Figure 7:
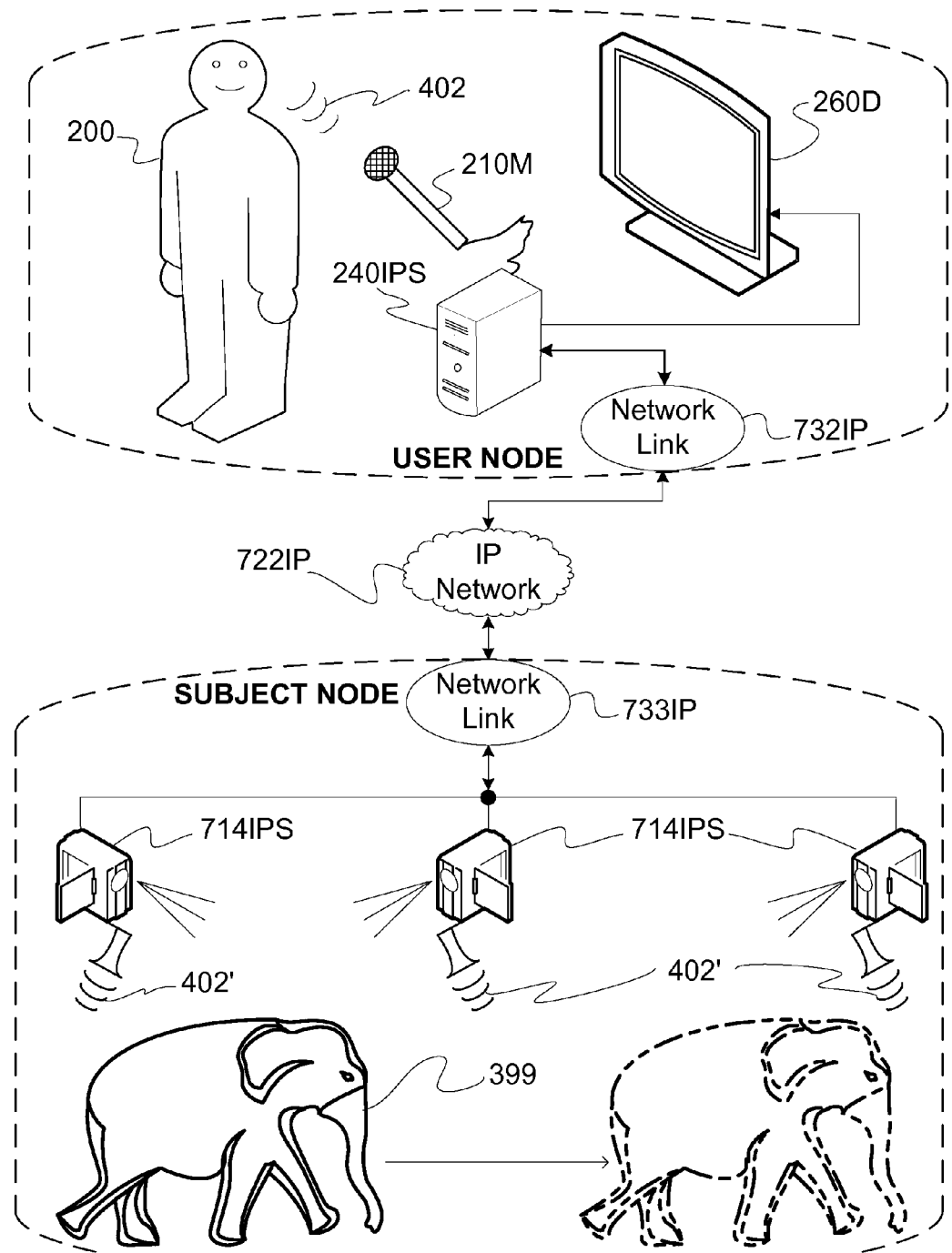
FIGS. 7, 7A, 7B, 7C, 7D, 7E & 7F show example embodiments for use where the example subject is an animal in a vast habitat and/or the subject node may lack internet access throughout.

Referring to FIG. 7, an example embodiment for the present case of using wireless internet (and/or wired, if available at the subject node) is shown. The user audience 200 at the user node observes the subject animal 399 on display means 260D. In this figure the example subject is illustrated as an elephant, an example of a subject which might have a wide-ranging habitat. Display means 260D can be a plurality of suitably sized and/or oriented display monitors or screens for the user audience. User node Network link 7321P operatively connects computing device 240IPS with or to the IP network 7221P (containing such inherent elements in the IP infrastructure as broadband modems, routers, WAP's, antennas, and other such elements). User node network link 7321P, which can be embodied by a network card in computing device 2401P for example, combines the functionality of a user node input link and user node output link, similar to user node network link 532 of FIG. 5A and other similar embodiments.

Computing device 240IPS can be the equivalent of computing device 240 of FIG. 2 with an operating system, input device drivers (including those for integrated or external audio devices), web browser, and programs including application software compatible with IP network cameras 714IPS, available either installed or commercially hosted or both. As is found in available security surveillance systems, wireless IP (or network) cameras are available with 2-way audio, and are shown particularized in the example figure as camera/speaker combinations 714IPS. The signals from the network cameras are transmitted through IP network 7221P to computing device 240IPS. The plurality of cameras 714IPS can vary, depending on the size of the habitat, obstructions, and effectiveness of embedded PTZ (Pan, Tilt & Zoom) capabilities, if any. The shown number of individual instances of cameras in any of the following figures varies and is arbitrary for illustrative purposes. The user audience in the present example communicates to the subject animal by emitting suitably audible sound signals 402 which are picked up by a microphone device 210M, either one of the user input devices integrated with the computing device or one of the external user input devices 210 in FIG. 2. The display means, similarly, can be integrated with the computing device but is shown here is illustrated an external display and can be one of the external user output devices 260 in FIG. 2. The sound signals 402 made by the user audience are transmitted through IP network 7221P to a plurality of the suitably amplified camera/speaker combinations 714IPS in proximity to the subject animal such that it perceives the emitted sounds 402'. The emitted sounds can be either a marker signal or a cue signal. In the case of a marker signal, as previously described in the context of other embodiments, these sounds can be verbalizations such as "Good boy/girl" or "Yes!" However, more precisely in serving as a distinctive marker signal to the subject animal, the user audience can directly make a unique sound (e.g., a clucking sound). Most precisely the user audience can use a device such as a metallic party clicker (a handheld device with a bendable noise producing flap), a whistle, horn or the like, operated in proximity to the microphone device 210M. In the case of a cue, the user audience chooses or directs the choice of a particular cue (such as the verbalization "sit" or "jump", for example) to be associated with a previously shaped behavior.

If internet access is not available, or the implementation of wireless internet coverage of a vast animal enclosure or zoo habitat otherwise is not practical, the following additional example embodiments can be used to realize the previously described methods.

Figure 7A:
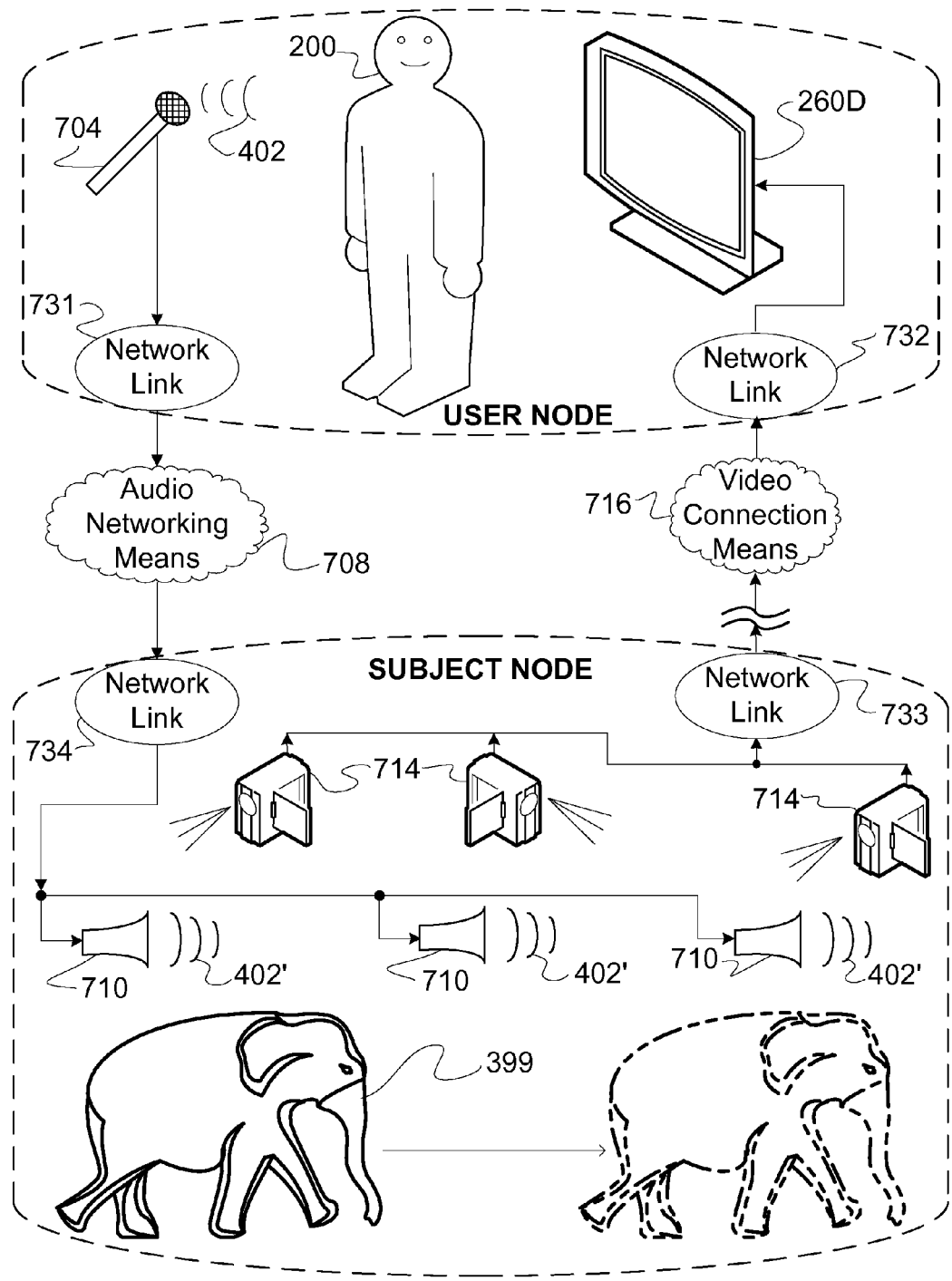

Referring to FIG. 7A, a high-level view of the present example is shown. The user audience 200 at the user node can be located at or near such an animal park or zoo, but at an intermediate safe distance from the subject animal habitat, and observes the subject animal 399 on display means 260D. Display means 260D can be a plurality of suitably sized and/or oriented display monitors or screens for the user audience.

User node network link 731 operatively connects with or to the audio networking means 708, User node network link 732 operatively connects with or to the video connection means 716, Subject node network link 733 operatively connects with or to the video connection means 716, and Subject node network link 734 operatively connects with or to the audio networking means 708. In the more particularized example embodiments to follow, any of the network links may be internal components of an explicitly illustrated device (i.e., an internal interface circuit in a telephone device, an internal network card with drivers in a computing device, internal sound or display card with drivers in a computing device, etc.).

The signals from the multiple camera video means 714 are transmitted through video connection means 716. The user audience selects the video signal which presently contains the subject animal in its point of view, this switching means to be shown and described in the next figure. The plurality of cameras in camera video means 714 can vary, depending on the size of the habitat, obstructions, and effectiveness of embedded PTZ (Pan, Tilt & Zoom) capabilities, if any. The shown number of individual instances of cameras illustrated in any of the following figures varies and is arbitrary, used only for illustrative purposes.

The user audience communicates to the subject animal by emitting suitably audible sound signals 402 which are picked up by a microphone device 704. These sound signals are transmitted through audio networking means 708 to a plurality of suitably amplified speaker devices 710 in proximity to the subject animal such that it perceives the emitted sounds 402'. The shown number of individual instances of speaker devices in any of the following figures varies and is arbitrary for illustrative purposes. As in previous embodiments, the emitted sounds 402' can be marker signals or cue signals, either verbalizations or other distinctively produced sounds.

Figure 7B:
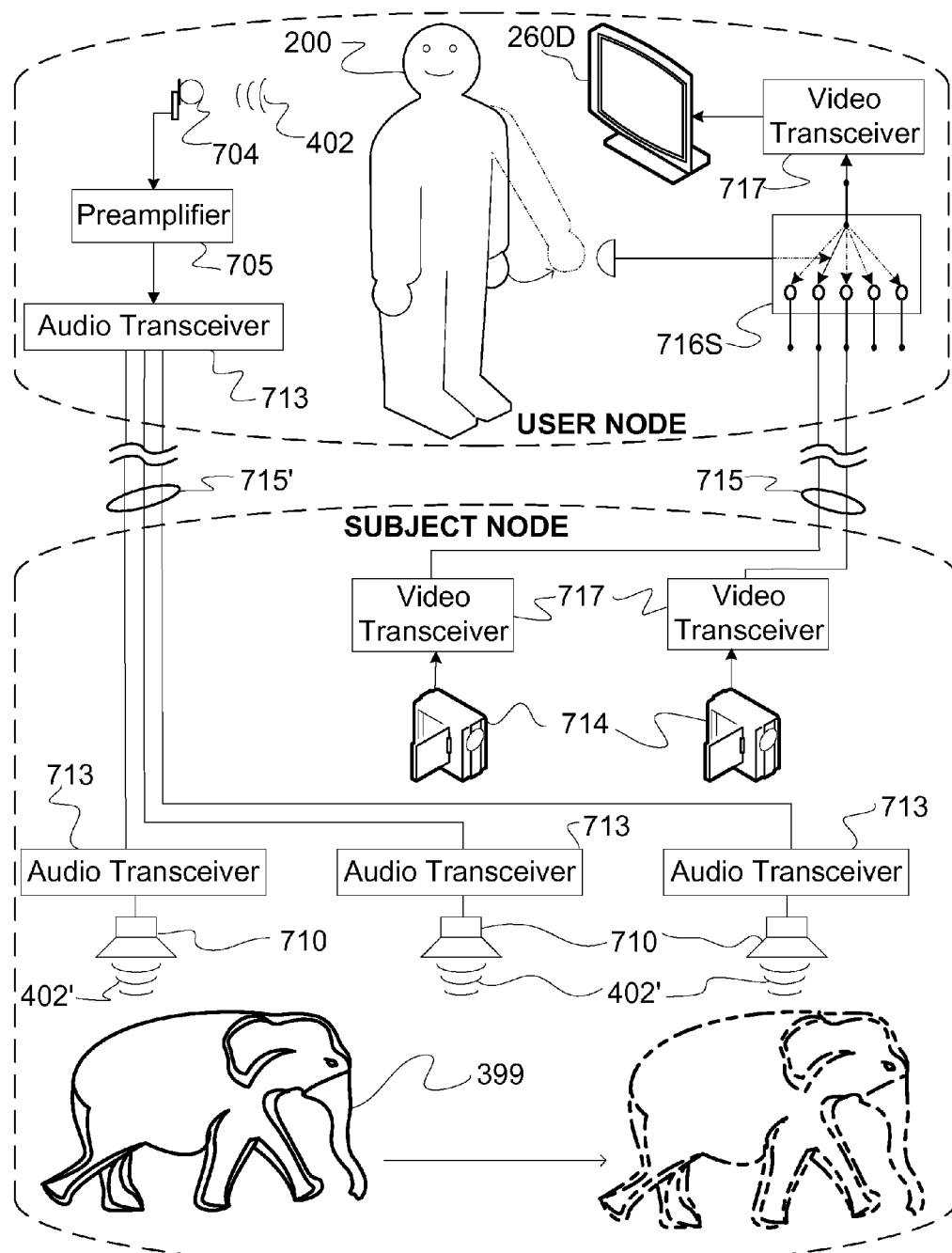

Referring to FIG. 7B, example embodiments of the audio networking and video connection means will now be described.

As previously discussed with reference to prior embodiment examples, where not explicitly illustrated, input and/or output network links are implicit in the configuration: i.e., a network link configured to interconnect with the PSTN network could be embodied by an RJ-11 jack (but not illustrated), a network link configured to interconnect with the internet (IP) network could be embodied by an RJ-45 jack (but not illustrated), a network link configured to interconnect with A/V cables could be embodied by Co-Ax connectors, RCA or component jacks, S-Video or HDMI connectors, etc., but not explicitly illustrated in a figure. Similarly, a network link configured to operate wirelessly could be embodied by an antenna but not explicitly illustrated, and so on.

At the user node the user audience observes the subject animal 399 at the subject node as it moves in its enclosure or habitat by switchably selecting which of the individual instances of video camera means 714 presently contains the subject animal 399 in its field of view. This is enabled by selecting an individual video channel, input to switching device 716S (commonly referred to as a multi-port AV Distribution or Switching Hub), and outputting that channel to the display means 260D. The cameras comprising the video camera means can be analog CCTV (Closed Circuit Television) cameras with the video cables 715 bridging the distance between the user node and the selected camera locations in the subject animal's enclosure or habitat. The video cables used for these intermediate distances can be UTP (Unshielded Twisted Pair) cables such as Cat5 (or higher) if, as shown in the figure, video transceivers 717 (also known as impedance transformers or "baluns"), are used at each end for impedance matching purposes. In this fashion, Composite, S-Video, Component Video, or other video formats (including digital formats such as VGA, RGB, or the like) can be transmitted over the distances involved. In other equivalent example implementations, composite video can be transmitted over coaxial cable, S-Video transmitted over S-Video, Component video transmitted over component cable, etc. In these cases the video transceivers 717 shown in the figure would not be used.

Still referring to FIG. 7B, an example embodiment of the audio networking means for communicating with the subject animal is shown. This particular embodiment uses cabling means for audio connections and so is a hard wired network. The user audience at the user node communicates to the subject animal by emitting suitably audible sound signals 402 which are picked up by a microphone device 704 operably connected to a preamplifier 705, producing line level audio signal. This signal is transmitted over audio cables 715' bridging the distance between the user node and a plurality of suitably amplified speaker devices 710 located in the subject animal's enclosure or habitat at the subject node. The audio cables used for these intermediate distances can be UTP (Unshielded Twisted Pair) cables such as Cat5 (or higher) if, as shown in the figure, audio transceivers 713 (also known as impedance transformers or "baluns"), are used at each end for impedance matching purposes. In this fashion, midrange audio formats can be transmitted over the distances involved. In other equivalent example implementations, audio can be transmitted over speaker wire, high end audio cable, or the like. In these cases the audio transceivers 713 shown in the figure would not be used. In the embodiment presently shown in the figure, the use of the UTP (Unshielded Twisted Pair) cables such as Cat5 (or higher) has the advantage of sharing conductor pairs in the same cable, such that video cable means 715 and audio cable means 715' can be embodied in the same multi-conductor cable, and both audio transceivers 713 and video transceivers 717 can be embodied in audio-video transceivers (combination A/V "baluns" which combine the functionality of both audio and video impedance transformers in a combination device). A plurality of suitably amplified speaker devices 710 are suitably distributed and located in proximity to the subject animal such that it readily perceives the emitted sound 402'. As in previous embodiments, these sounds can be marker signals or cue signals, either verbalizations or other distinctively produced sounds.

Figure 7C:
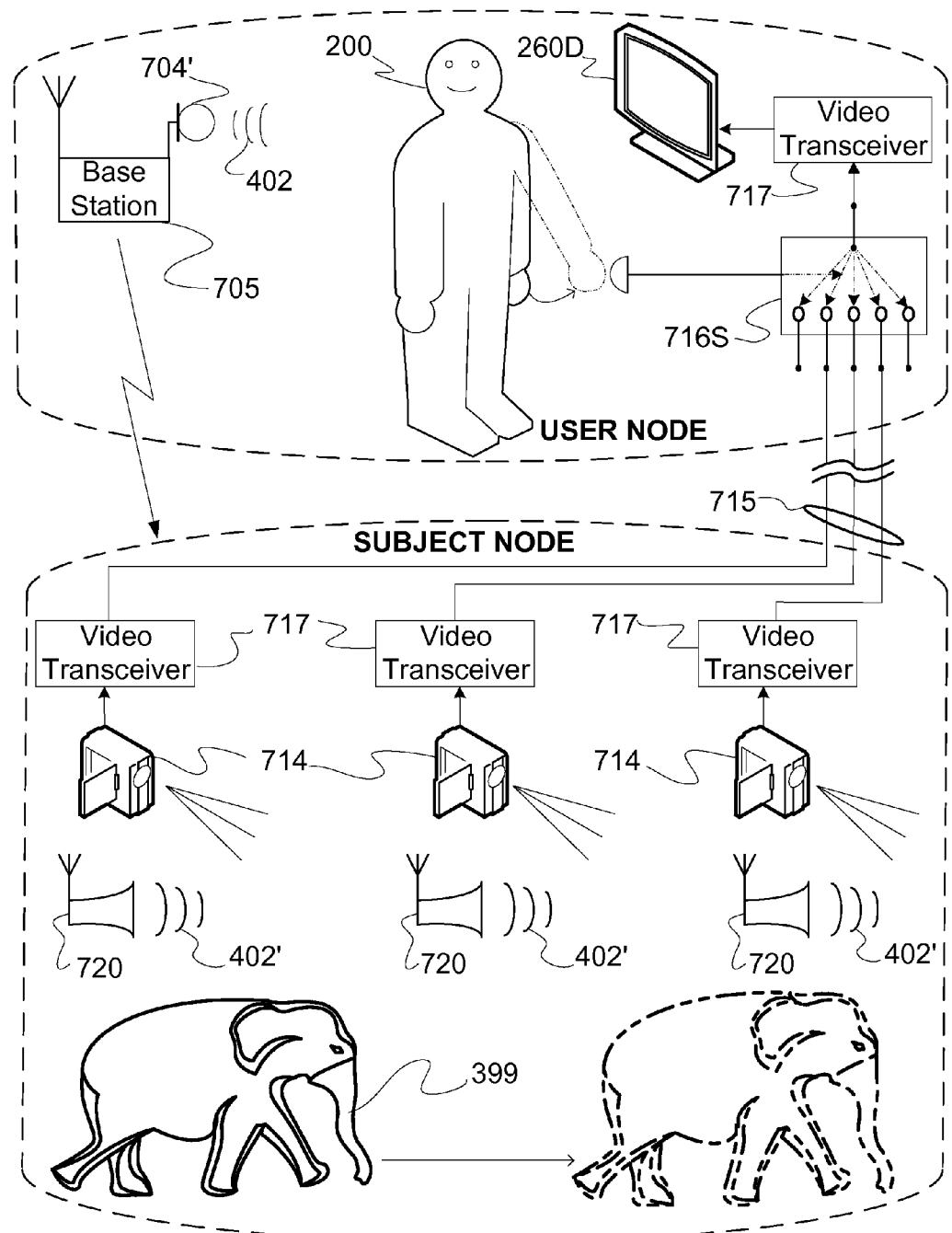

Referring to FIG. 7C, an additional example embodiment is shown for the audio networking means between user and subject nodes. In this example, the user audience communicates with the subject animal using wireless means. At the user node the user audience 200 communicates to the subject animal 399 by emitting suitably audible sound signals 402 which are picked up by a microphone device 704' operably connected to or incorporated within a two-way radio or wireless intercom base station 705. These sound signals are transmitted over the wireless radio or intercom frequencies to one or more wireless PA speaker devices 720. These wireless PA speaker devices, or equivalently, intercom system "Callboxes", available for outdoor use at property gates and the like, are suitably distributed and located in proximity to the subject animal such that it readily perceives the emitted sound 402'. As in previous embodiments, these sounds can be marker signals or cue signals, either verbalizations or other distinctively produced sounds.

Figure 7D:
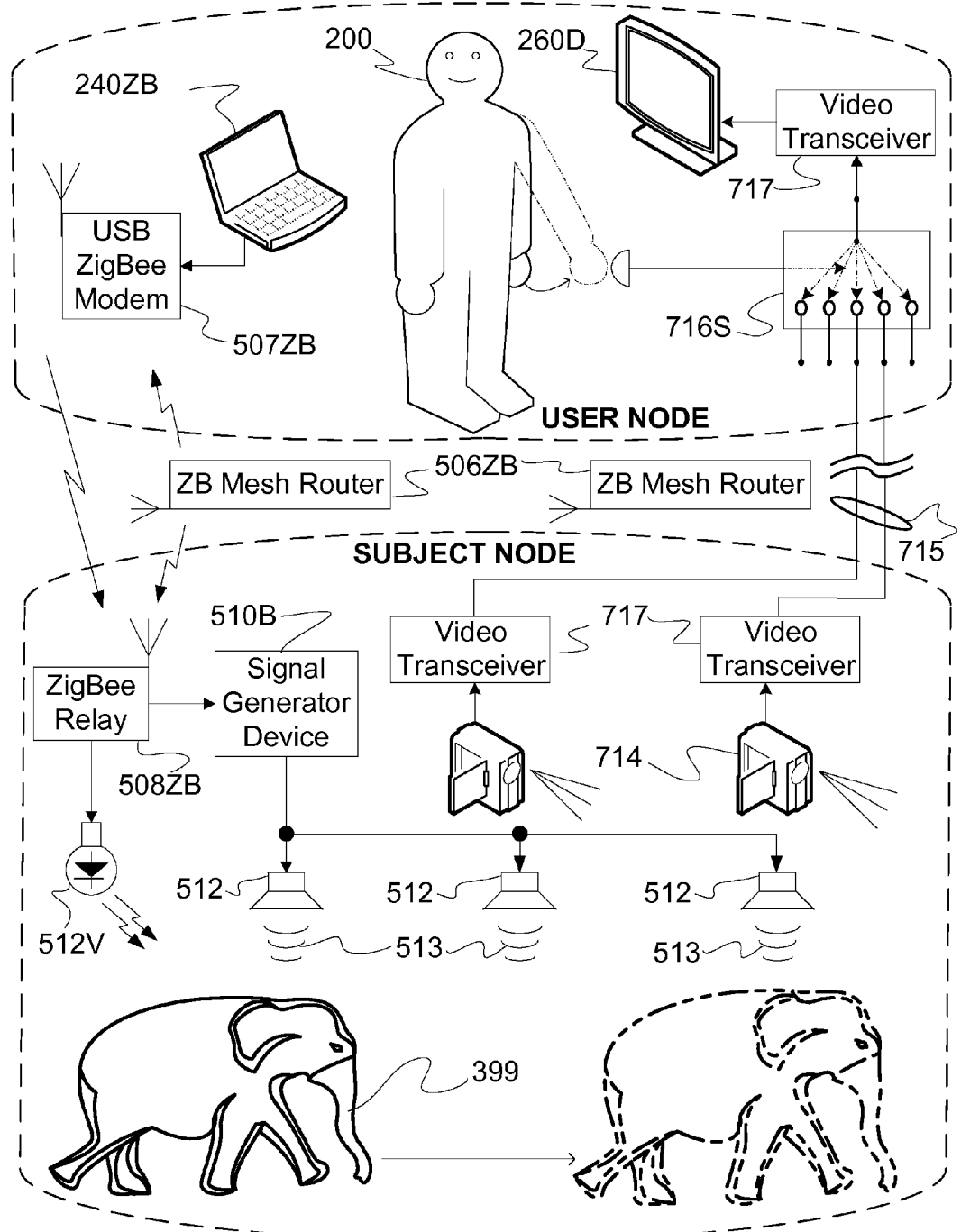

Referring to FIG. 7D an additional example embodiment is shown for the audio networking means between user and subject nodes using wireless means. The wireless example illustrated herein is the ZigBee suite of protocols (based on the IEEE 802.15.4 standard) but any radio specification for wireless personal area networks (WPAN's) would enable the example embodiment with the same functionality in substantially the same way to achieve the same result. At the user node the user audience 200 uses the computing device 240ZB as a switching device. The computing device 240ZB can be the equivalent of computing device 240 of FIG. 2 (shown here with an integrated display) with an operating system, input device drivers, and programs including application software compatible with ZigBee Relay 508ZB. This software is available either installed or commercially hosted or both. This programming enables the computing device 240 to function as a switching device wherein the user audience uses a mouse, keyboard or other user input device (either one of the integrated or one of the external user input devices 210). The computing device 240ZB, when so used, acts responsively to user input to communicate a command to the USB ZigBee Modem 507ZB. The modem then communicates wirelessly to the ZigBee Relay 508ZB at the subject node to energize it. If the subject animal's habitat is such that the ZigBee Relay is out of the wireless range of ZigBee modem 507ZB, a ZigBee Mesh Router 506ZB can be positioned between the modem and relay and used to bridge the gap in coverage. A ZigBee Mesh network can so be built, using as many such ZigBee Mesh Routers as needed, placed around the periphery of the subject animal's habitat and/or within it if necessary. When the relay 508ZB energizes and closes it contacts, the signal generator device 510B is powered and generates an audio signal as previously described with reference to prior embodiments. Suitably amplified speaker means 512 is located in proximity to the subject such that the emitted sound 513 is readily perceived by it as a known marker (or cue) signal. The speaker means 512 can be a suitably located plurality of suitably amplified speaker devices if needed. In addition to an acoustic transducer, the example effectuation of a visual signal is again illustrated as example visual signal source 512V which is energized by ZigBee Relay 508ZB. For the type of subject in the current particular embodiment, the alternate example of assembly 512V' depicted in FIG. 5A may also be appropriate to effectuate a visual signal, i.e., actuating a sign or flag or the like in such a way that it is visible to the subject. As with acoustic signals, the generated visual signals can serve as marker signals or cues to the subject.

A plurality of ZigBee Relay/Signal generator device combinations can be used, and addressed as a group or selectively in the mesh using the ZigBee compatible programming with computing device 240ZB, therefore enabling different marker signals for different animals within the same habitat. This same selectivity which enables the delivery of a variety of signals also enables the use of some of them to serve as predefined cues to a subject animal. Therefore, the example embodiment serves to provide a variety of cues as well as a variety of marker signals.

Figure 7E:
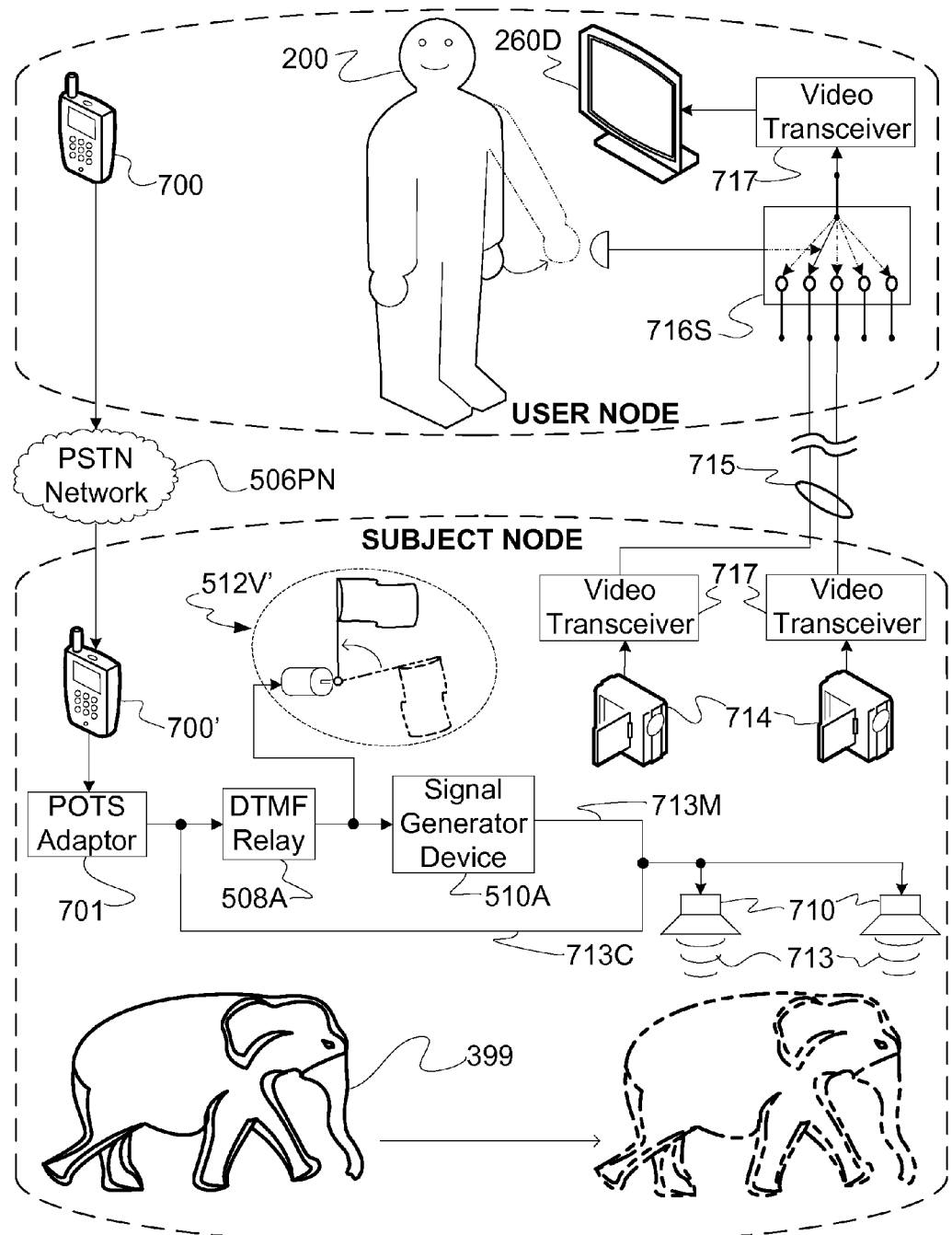

Referring to FIG. 7E, an additional embodiment is shown using audio means for communicating with the subject animal if at the subject node the animal enclosure or habitat at the animal park or zoo has cellular phone coverage. A plurality of suitably amplified speaker devices 710 is suitably located in the subject animal's habitat. At the user node, as previously described with reference to prior embodiments, a DTMF (Dual Tone Multi Frequency or "Touch-Tone", also known as tone-dialing) capable cellular phone 700 communicates over the PSTN (Public Switched Telephone Network) 506PN and is used by the user audience 200 as a switching device. The call is placed to a second cellular phone 700' at the subject node in or near the subject animal's enclosure or habitat. This cellular phone is connected to a POTS (Plain Old Telephone System) Adaptor 701 (also referred to as a Cell Phone to POTS Adaptor, Cell Phone Adaptor, or Socket Adaptor). This connection can be made by cable or wirelessly by a Bluetooth connection. The output of the POTS adaptor 701 is input to DTMF Relay 508A (the connection most commonly being made via standard RJ-11 phone jacks and cord). The relay is energized when the user audience enters preprogrammed digits on the telephone. A signal generator device 510A, activated by the DTMF relay, generates a signal, for example an audio marker signal 713M. This signal generator device can be any distinctive noise producing device such as a buzzer, chime, horn, etc. Although described here as generating a single tone, whistle, chirp or the like, the signal generator device 510A can be a switched plurality of tone (or waveform) generating circuits or similarly a selectably tunable waveform or tone generator. The suitably amplified speaker devices 710 are located in the subject animal's habitat such that the audio signal 713M is amplified so that emitted sound 713 is readily perceived by the animal, for example as a known marker signal (or a cue signal—however, see below for another implementation allowing for the generation of cue signals in the present example).

In addition to an acoustic transducer, the example effectuation of a visual marker signal (or, additionally, cue signals) such as the example visual source 512V' (previously described as the actuation of a flag or sign) is shown, energized by DTMF Relay 508A.

In addition to the above marker signal, audible cues in the form of verbalizations also can be generated for the subject animal. Still referring to FIG. 7E, the audio output of the POTS Adaptor 701, marked as signal 713C, can also be fed to the suitably amplified speaker devices 710 (or different amplified speaker devices, if desired), thereby allowing any vocalizations into cellular phone 700 to be amplified such that the resulting emitted sound 713 can be used by the user audience as a cue. Further, the example effectuation of a visual cue signal such as the example visual source 512V (or 512V') illustrated in prior embodiments could be used, energized by DTMF Relay 508A.

Figure 7F:
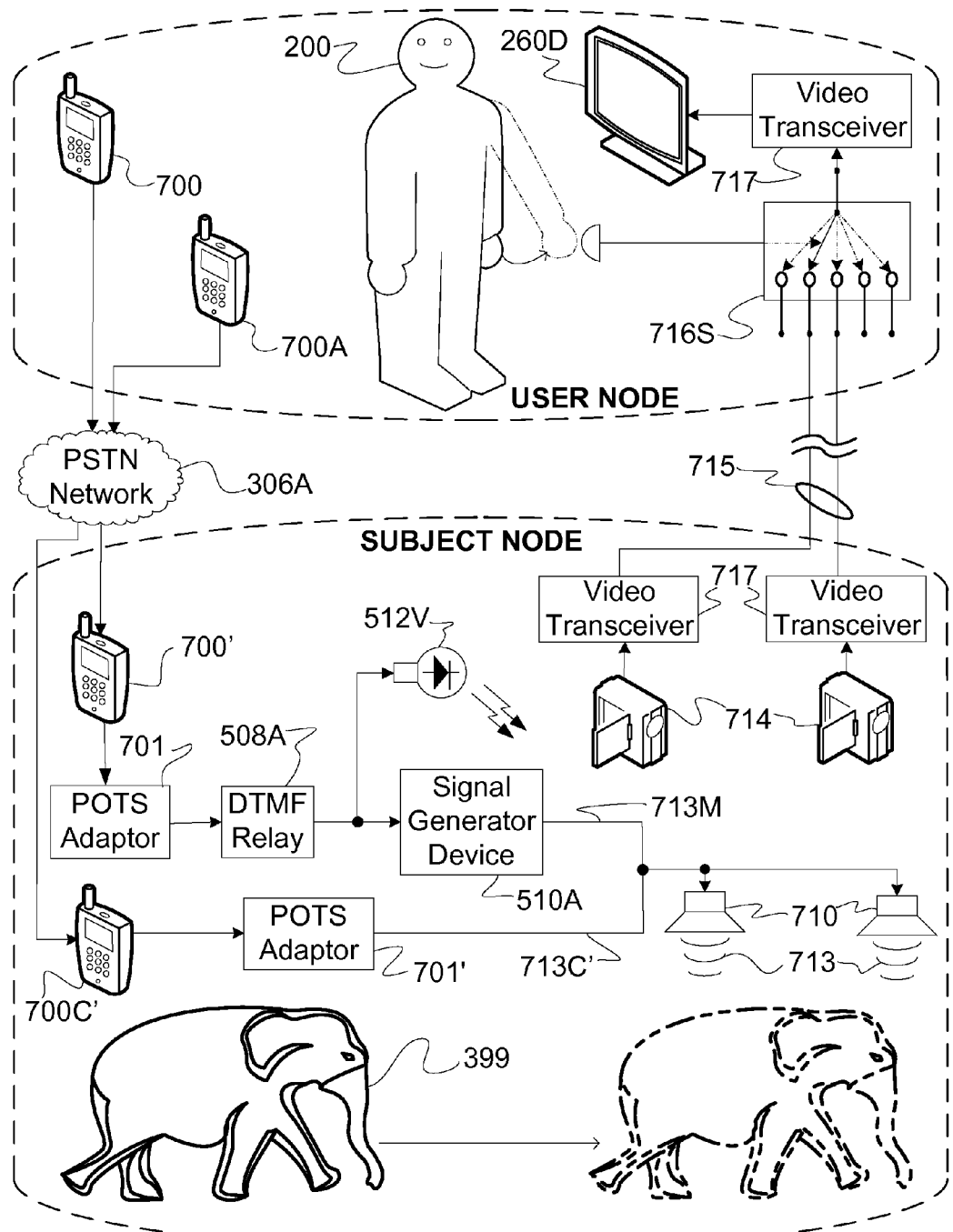

Referring to FIG. 7F, another example embodiment of audio means to generate an audible verbalized cue signal is shown. A second cellular phone 700C' in or near the subject animal's enclosure or habitat at the subject node can also be used to produce a cue to the subject animal. This cellular phone is connected to a second POTS Adaptor 701' in a similar manner to that described above, and its output audio signal 713C' is amplified by suitably amplified speaker devices 710 such that the resulting emitted sound 713 can be used by the user audience as a cue. Further illustrated is the example effectuation of a visual cue signal such as the example visual source 512V as used in prior embodiments, energized by DTMF Relay 508A.

If the user audience does not wish to use a single cellular phone to generate both marker signals and cues to the subject animal, preferring to use one as a switching device to generate marker signals and the other to transmit verbal cues, a second cellular phone 700A at the user node can be used by the user audience. This could also be used to increase classroom participation in an educational setting or audience participation in an entertainment setting. In this particular embodiment of audio means, the user audience then would use one of the cellular phones 700 or 700A to dial cellular phone 700', for example, and generate a marker signal by pressing digits to send pre-preprogrammed tones. The user audience would then use the other cellular phone to dial 700C', for example, and vocalize cues to the subject animal. Further illustrated is the example effectuation of a visual cue signal such as the example visual source 512V as used in prior embodiments, energized by DTMF Relay 508A.

As previously discussed, a marker signal marks a desired behavior or event precisely in time by virtue of being a conditioned positive reinforcer, in that the subject animal associates it with a primary reinforcer—in other words, it has learned a primary reinforcer is coming when it hears (or senses) the conditioned reinforcer. Embodiments described here will focus on delivery of a food treat as the primary reinforcer at the subject node.

A handler or keeper at the subject node can enable delivery of a food treat as a primary reinforcer in response to the marker signal given to a subject animal in a variety of ways, depending on whether or not the animal is safely handle-able and the qualifications of the handler. The animal can be hand fed, given food on a stick, from either within its enclosure or through a relatively small opening, receive food delivered through a trap door, long tube or similar geometry which isolates the keeper from the animal, have food thrown into its enclosure or habitat, or other similar method. For animals in relatively vast enclosures or habitats, a means of delivering the food remotely following the marker signal may be particularly advantageous. This delivery can be done manually in response to the marker signal or in an automatic fashion. Depending on the habitat size, terrain, perimeter fencing, type of animal, and food, it might be advantageous to employ not only a plurality of remote means, but also a suitable variety of these means in various combinations.

Figure 8A:
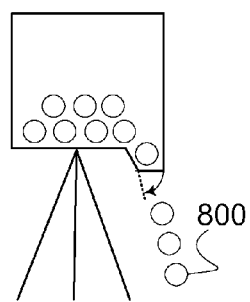
FIGS. 8A, 8B, 8C & 8D show example embodiments for delivery of a primary reinforcer at the subject node.
Figure 8B:
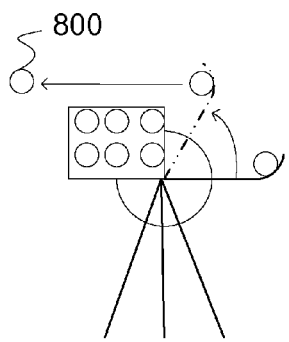
Figure 8C:
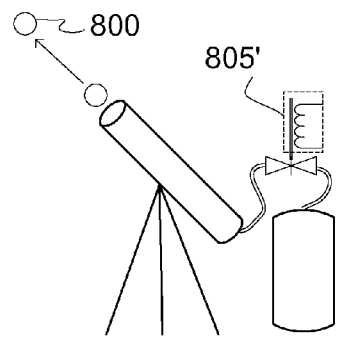

Referring to FIGS. 8A, 8B, & 8C, embodiments of varied means for remotely delivering food treats as a primary reinforcer following a marker signal will be described. Shown in the figures are devices dispensing food pellets 800. FIG. 8A shows a game feeder used to dispense food, FIG. 8B a pitching machine used to throw food, and FIG. 8C an air cannon device used to shoot food.

Referring to FIG. 8A, game feeders such as that shown are typically available in hanging or freestyle configurations and so can be located in the habitat and/or on the perimeter. Such game feeders are often designed to operate and dispense food on timers, but are also often available with an add-on wireless remote control accessory. The wireless signal sent when the user presses a button energizes a relay in the feeder, temporarily actuating the motor or other actuator that dispenses the food.

Referring to FIG. 8B, pitching machines such as that shown are typically spring loaded arm pitching machines normally used for throwing baseballs, softballs, wiffle balls, and/or tennis balls. They can be used for throwing fruit to the animal, including but not limited to spherical fruits like oranges and grapefruits. Pitching machines can also be activated by a remote control.

Referring to FIG. 8C, air cannon devices such as that shown are also known as "spud guns" or "potato cannons", perhaps as an indication of their possible origin in use to shoot potatoes to bears in forests. Air cannon devices are typically used to shoot promotional items such as T-shirts or hot dogs at sporting events and the like and have been used on an annual basis in pumpkin throwing contests in the United States. They are typically powered by CO2 or compressed air. Valves in pneumatic versions admitting pressure to the barrel or firing cylinder are available as electronic solenoid valves (or can be replaced with such solenoid valves), shown as solenoid valve 805'.

Upon hearing the marker signal, a handler or keeper at the subject node can manually actuate an accessory remote control accessory unit with the devices described above to actuate them and deliver food in response to hearing the marker signal. Instead of or in addition to manually operating accessory remote control units, an automatic food delivery means in response to the marker signal will now be described.

Figure 8D:
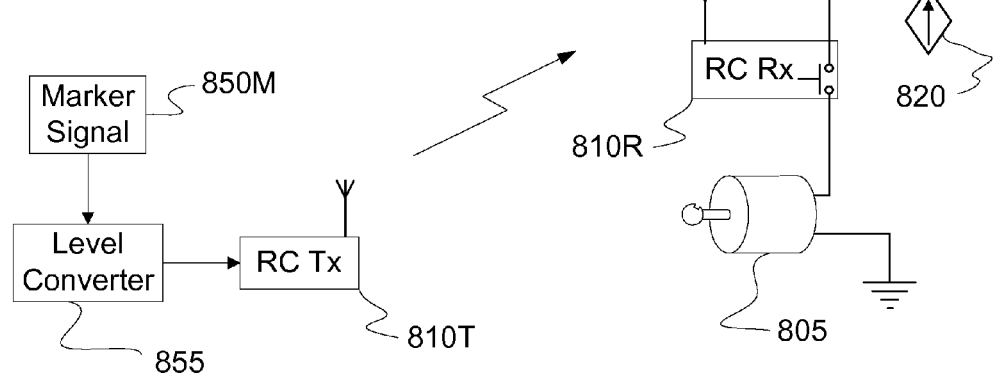

Referring to FIG. 8D, a wireless remote control transmitter/receiver pair can enable this functionality. A wireless remote control receiver 810R which contains internal relay contacts can replace or operate in parallel with an embedded accessory remote control unit in the food delivery device. This wireless remote control receiver is installed in or near the food delivery device and receives a signal from compatible wireless remote control transmitter 810T. When this signal is received by receiver 810R, the receiver closes its internal relay contacts, allowing current to flow from a device power source 820 and through motor or actuator 805 (or solenoid valve 805' in the case of the air cannon in FIG. 8C), thereby energizing the actuator and dispensing or projecting the food. The transmitter 810T can be used as a remote control manually operated by a switch on the unit (not shown) in response to hearing the marker signal, or in an automatic mode by transmitting in response to the electrical marker signal 850M. The voltage level of the electrical marker signal 850M can be converted by level converter 855 to a level compatible with and sufficient to switch transmitter 810T (this could be effected, for example, by a relay whose coil is energized by the electrical marker signal 850M and whose output contacts connect a suitable voltage supply to transmitter 810T).

In the example embodiments shown for a large enclosure or habitat, for example, the electrical marker signal 850M would be the output of the DTMF Relay 508A (of FIGS. 7E & 7F) or ZigBee Relay 508B (of FIG. 7D). Equivalently, if wireless internet access is available, as previously discussed the previous example embodiments utilizing the IP network could be used in the same manner in which case the electrical marker signal 850M could be the output of the Web Relay 5081P of prior embodiments. Other equivalent implementations are available for generating equivalents to electrical marker signal 850M such as using outputs of the signal generator devices 510A or 510B or direct acoustic detection of the audible marker signals.

In this manner, food (as a primary reinforcer) is dispensed automatically at the subject node after the animal has been given a marker signal (a conditioned reinforcer). Other functionally equivalent devices serving as automated food delivery means can be centrifugal spinning devices, various other catapult devices such as trebuchet sling devices, etc.

Figure 9:
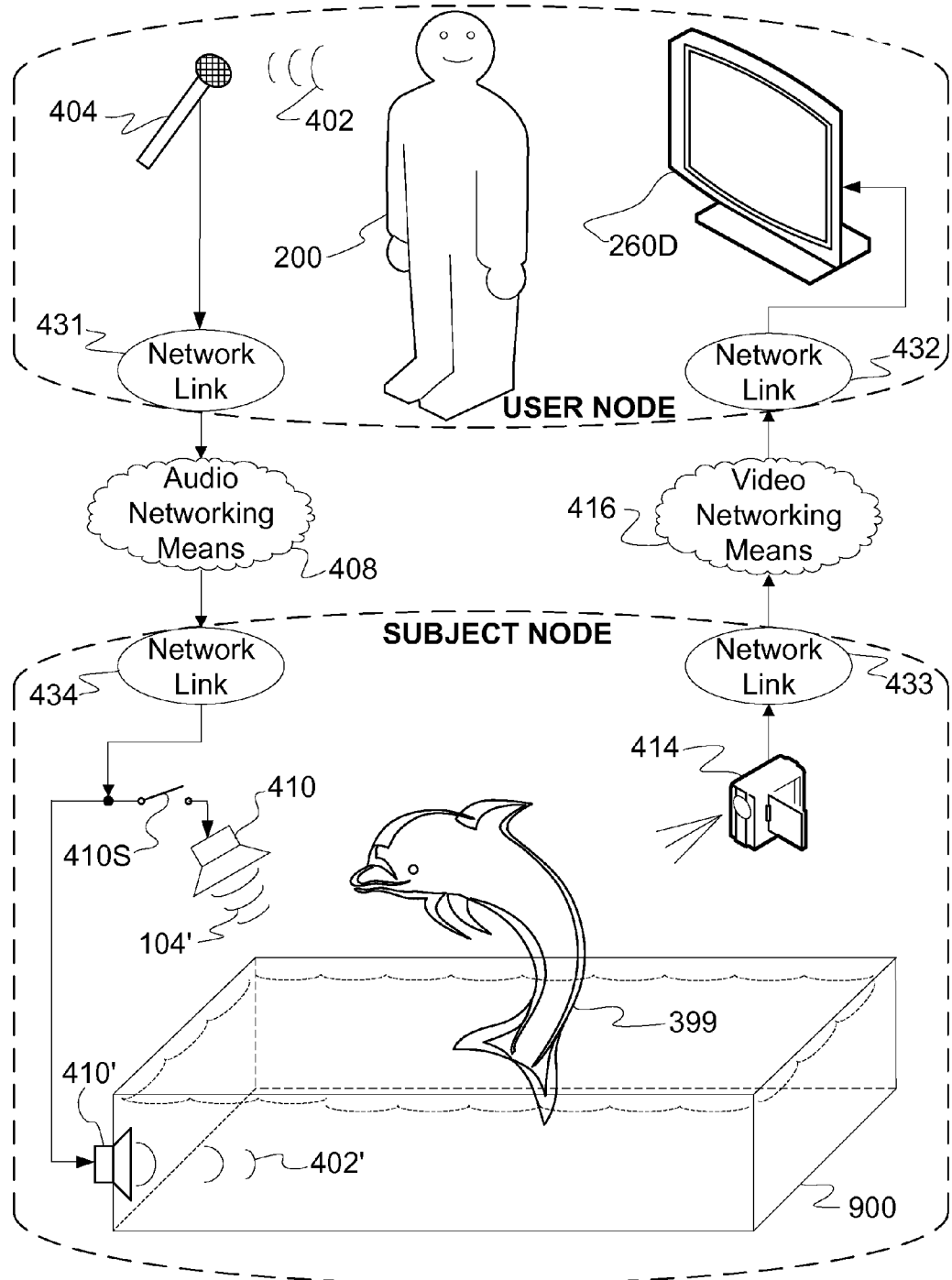
FIGS. 9, 9A & 9B show example embodiments for use where the example subject is an aquatic animal and/or the subject node is an aquarium.
Figure 9A:
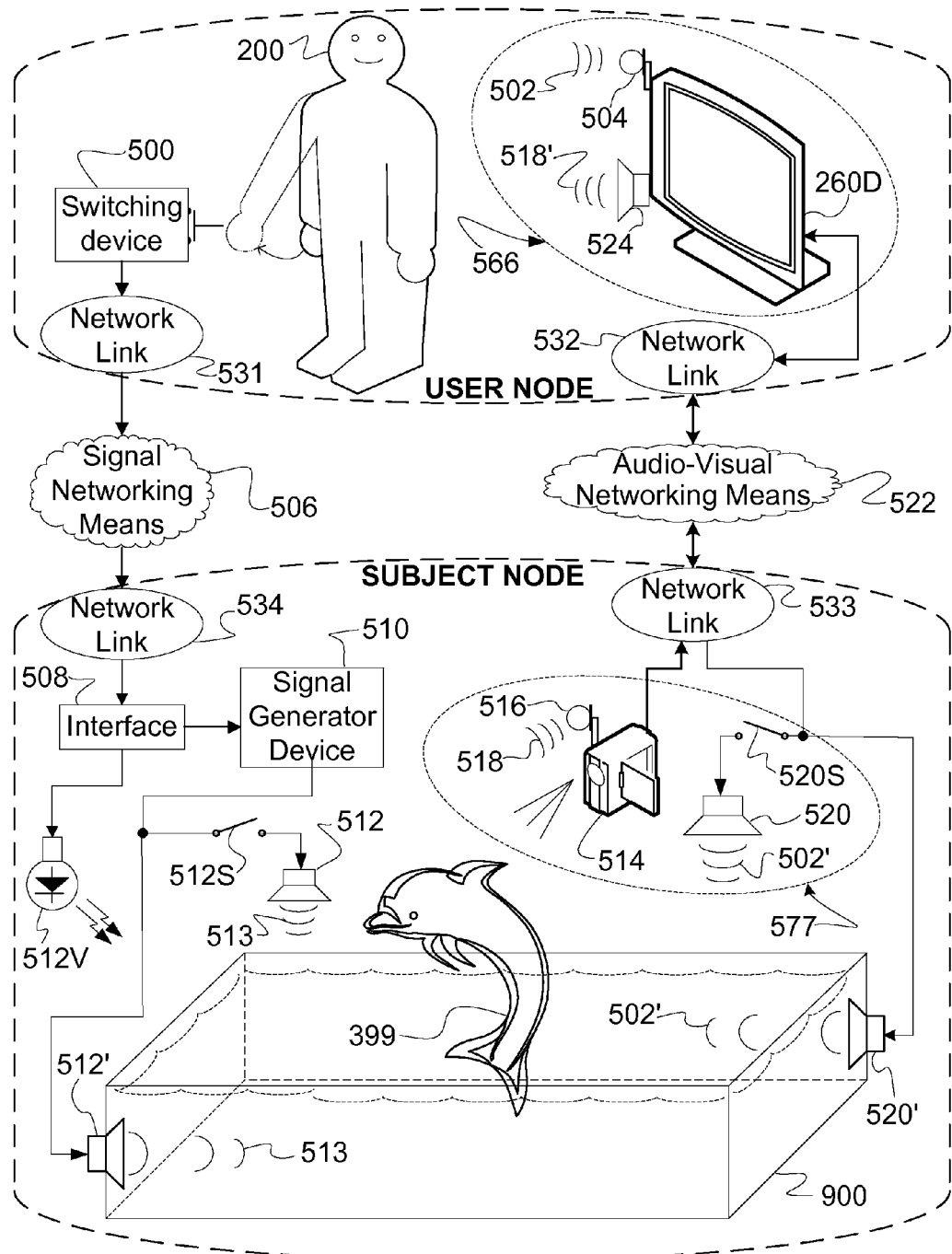
Figure 9B:
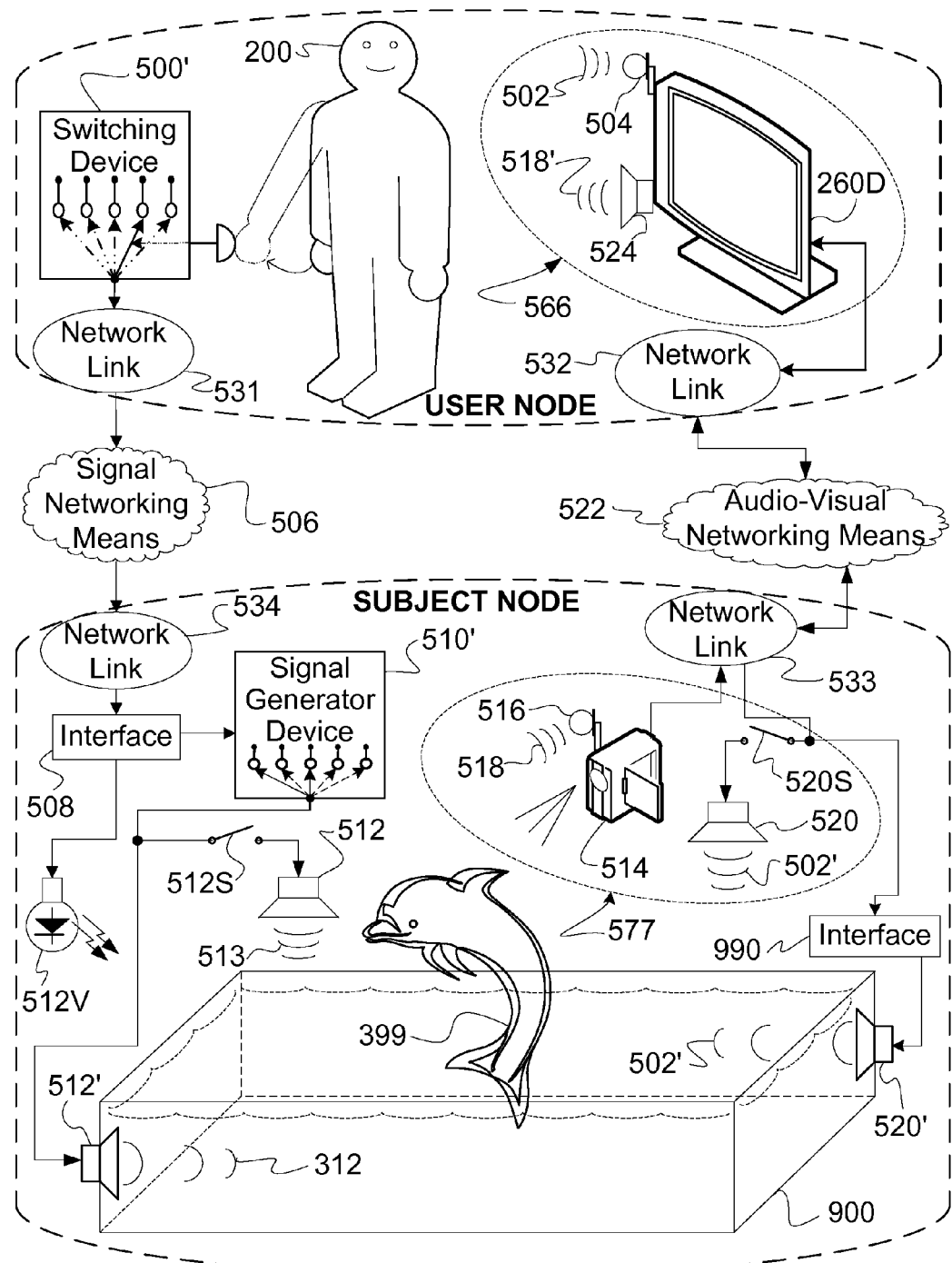

Additional example embodiments for use where the subject is an aquatic animal are shown in FIGS. 9, 9A & 9B. The subject animal 399 is shown as an aquatic animal in a pool of water 900. Underwater tones are often used with aquatic animals, in particular marine mammals such as dolphins, whales, porpoises and the like.

Referring to FIG. 9, all of the microphone, speaker, camera and display means, network links, audio networking means and video networking means equivalent to those shown in FIG. 4A are shown, but with speaker means 410 also shown as an underwater speaker 410'. The speaker device 410 as originally shown (above water) is now shown optionally switched on or off via switch 410S.

Referring to FIG. 9A, all of the switching, interfacing, signal generating, microphone, speaker, camera and display means, network links, signal networking means and audio-visual networking means equivalent to those shown in FIG. 5A are shown but with speaker means 512 and 520 also shown as underwater speakers 512' and 520' respectively. The speaker devices 512 and 520 as originally shown (above water) are now shown optionally switched on or off via switches 512S and 520S respectively.

As in prior embodiments, in addition to an acoustic transducer, the additional example of effectuating a visual signal is illustrated as example visual signal source 512V which is energized by interface 508. For the type of subject in the current particular embodiment, the alternate visual example of assembly 512V' depicted in FIG. 5A may also be appropriate to effectuate a visual signal, i.e., actuating a sign or flag or the like in such a way that it is visible to the subject. As with acoustic signals, the generated visual signals can serve not only as marker signals but also as cues to the subject.

Referring then to both FIGS. 9 & 9A, it follows that all of the example embodiments previously described with reference to, detailing and flowing from FIGS. 4A and 5A can be used in the same manner as previously described, including the example operations of the embodiments described in FIG. 11 (shaping a behavior), FIG. 12 (bringing a shaped behavior under cue control), and FIG. 13 (operantly shaping and/or demonstrating behavior chains). Thus, using the embodiments herein, aquatic animals can be operantly conditioned in the same interactive manner as previously described, with the same educational and entertaining results.

Additional uses of the embodiments shown for aquatic subject animals that are already trained with predetermined audible cues will now be described. For example, in the case where the aquatic subject animal is already trained to recognize predefined certain underwater tones as cues, the operant conditioning and/or demonstration of behavior chains (for example as described in FIG. 13) can be implemented using the embodiments described.

Referring to FIG. 9B, the switching device 500 of FIG. 9A (and FIG. 5A) is now illustrated with more detail as switching device 500' and signal generator device 510 of FIG. 9A (and FIG. 5A) is now illustrated with more detail as signal generator device 510'. At the user node, the user audience operates the switching device 500' to selectably switch the desired tone (or composite of tones). The signal generator device 510' can be a switched plurality of tone (or waveform) generating circuits or similarly a selectably tunable waveform or tone generator. The switching devices and signal generators can be used to generate predetermined tones in selectable fashion, so that the emitted sounds 513 are used as predefined cues to the aquatic subject animal (in addition to or instead of as marker/conditioned reinforcer signals). In the example embodiments previously described in FIGS. 5B & 5C, and FIGS. 5J & 5K, telephones are used as switching devices with DTMF relays 508A used as the interfaces. In FIGS. 5D & 5E, web relays 5081P are used as the interfaces. Both DTMF relays 508A and web relays 5081P contain multiple output channels (if the number of output channels is not sufficient they can be paralleled or grouped). These relay outputs open and close selectively in response to varied pre-programmed touch-tone digits or computer inputs. Therefore both the DTMF relays 508A and web relays 5081P shown in the prior embodiments can selectably energize different waveform or tone generating circuits of the signal generator devices 510A or 510B shown in the previous example embodiments. Similarly, the ZigBee Relay 508ZB shown in the previous example embodiments has multiple selectable channels, as well as other prior example embodiments (e.g., Home Automation, Bluetooth embodiments). These relay outputs can therefore selectably energize different waveform or tone generating circuits of the signal generator device 510'. Thus, varied pre-programmed tones can be produced such that the emitted sounds 513 are known predefined cues to the aquatic subject animal (in addition to or instead of as marker/conditioned reinforcer signals). A particular one of the emitted tones (a whistle tone for example) can be used as a marker signal recognized by the aquatic subject animal. Alternatively, the emitted sounds 502' at the subject node can be used as a marker signal by the user audience if a device such as a whistle, for example, is used to produce sound 502 at the user node. Further, the user audience can verbalize a sound 502 as a verbalized cue ("SPLASH" for example).

As in prior embodiments, in addition to an acoustic transducer, the additional example of effectuating a signal is illustrated as example visual signal source 512V which is energized by interface 508. For the type of subject in the current particular embodiment, the alternate visual example of assembly 512V' depicted in FIG. 5A may also be appropriate to effectuate a visual signal, i.e., actuating a sign or flag or the like in such a way that it is visible to the subject. As with acoustic signals, the generated visual signals can serve not only as marker signals but also as cues to the subject.

If the marine park or aquarium at the subject node has its own internal auditory cueing system, an onsite marine animal handler can still enable the user audience at the user node to provide cues to the animal, providing the same interactive, educational and entertaining benefits previously described, such as with the operant conditioning and/or demonstration of a behavior chain. The user audience gives the animal a cue (for example, "SPLASH"). The corresponding known auditory cue for that behavior can be delivered to the animal through Interface 990 which can take several forms:

A "MIL" ("Man-In-the-Loop") Interface: The onsite marine animal handler at the subject node, upon hearing the verbalized cue 502' (with switch 520S closed), responsively enters the corresponding codes or commands on the park or aquarium's auditory cueing system and the underwater cue 502' known to the animal (for "SPLASH", for example) is effected. In this scenario, speaker 520 can be a headset worn by the onsite marine animal handler, with microphone 516 also worn and used to transmit instructions or explanations to the user audience if necessary. Marker signals can be given by user audience using the switching device 500' at the user node as described in the previous embodiments.

Alternatively, Interface 990 can be an electronic interfacing circuit which accepts either sounds or other inputs from the user audience (effected by one of the previous prior example methods) and outputs either the predefined auditory cues known to the aquatic animal or the input codes in a compatible format for the marine park or aquarium internal cueing system.

Modes of Operation

Figure 10:
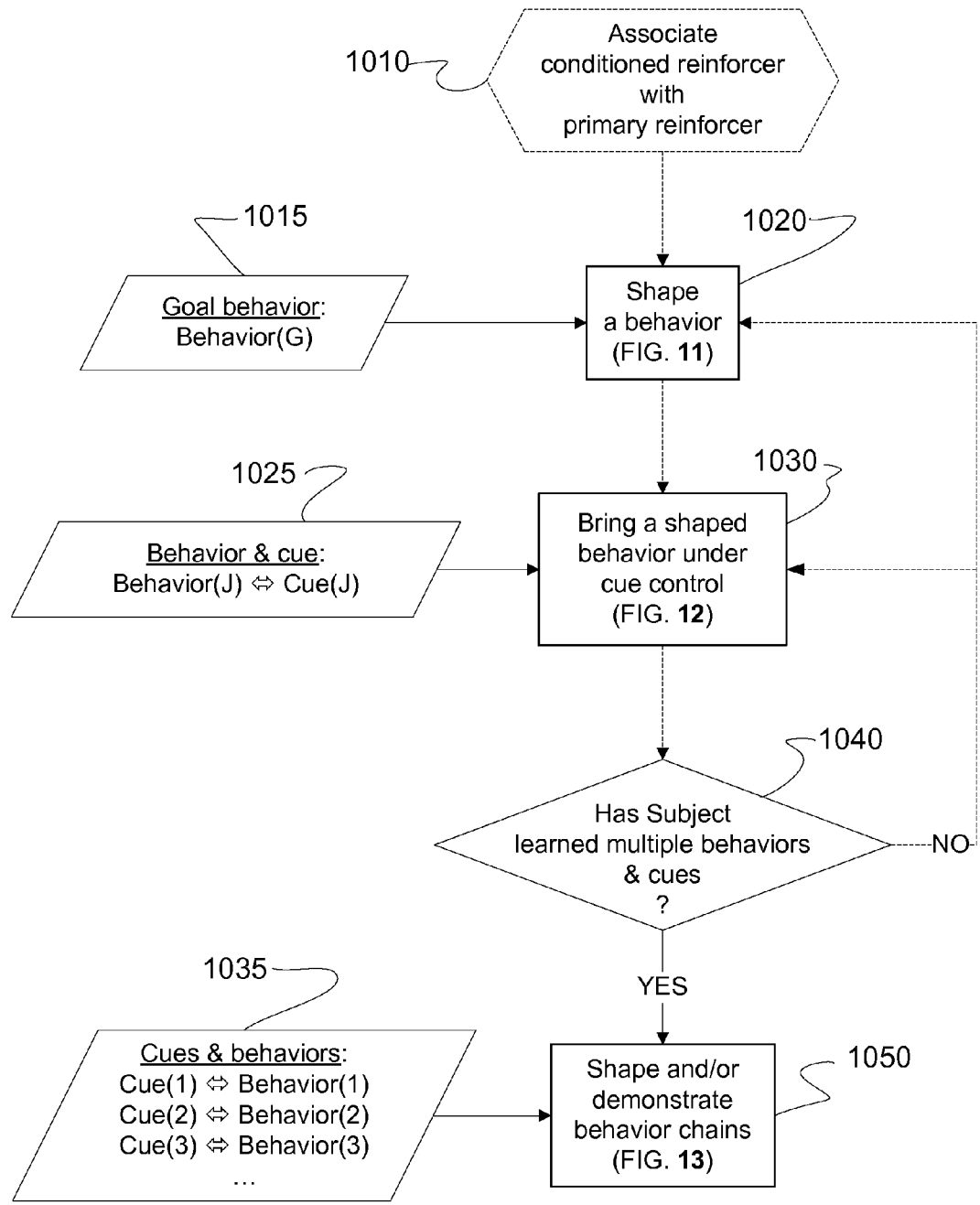
FIG. 10 is a high-level illustration of some example modes of operation of the embodiments.

Referring to FIG. 10, shown are examples of modes of operation of the various embodiments. Each of the general steps 1020, 1030, or 1050 can represent an operant conditioning session between a user audience and a different example subject at a different example subject node, and so the steps shown do not need be followed in the sequence shown, although if the embodiments are used by the same user audience for the same subject at the same subject node the sequence shown could be a logical progression for the subject. Different steps in and of themselves may have differing degrees of educational purpose and/or entertainment value, or may be used strictly for therapeutic behavioral modification (such as operantly conditioning a child for toilet training, a mentally challenged person for personal hygiene, self-feeding or dressing, reducing self-injurious behavior, etc.).

Step 1010 (Associate conditioned reinforcer with primary reinforcer)—This step depicts associating a conditioned reinforcer with a primary reinforcer (or unconditioned reinforcer, something always wanted by the subject, such as food or the opportunity to play). If the subject is a child, for example, then the primary reinforcer might be a piece of candy. If the subject is a dolphin, for example, the primary reinforcer might be fish. A conditioned reinforcer can be any signal which can be sensed by the subject indicating to the subject that the primary reinforcer is coming: a whistle preceding a fish, a clicking sound preceding some candy, etc. For example, for a classroom of children the recess bell is a conditioned reinforcer through its association with a primary reinforcer (the opportunity to play). Different example subjects, whether at the same or different subject nodes, can have different conditioned reinforcers established and predefined.

Step 1020 (Shape a behavior)—This step depicts using the example embodiments to operantly shape a behavior. A predefined behavior shown as Behavior(G) in step 1015 is chosen or selected by the user audience and used as a goal (see FIG. 11).

Step 1030 (Bring a shaped behavior under cue control)—This step depicts operantly shaping a behavior to be under cue control for a subject in which at least one behavior has already been shaped, the particular behavior shown as Behavior(J) in step 1025. The user audience selects a predefined cue shown as Cue(J) corresponding to the selected shaped Behavior(J) (for example, "SIT" for a sitting behavior) (see FIG. 12).

Step 1050 (Shape and/or demonstrate behavior chains)—This step depicts operantly shaping and/or demonstrating behavior chains for a subject in which several behaviors are already under cue control (see FIG. 13).

Figure 11:
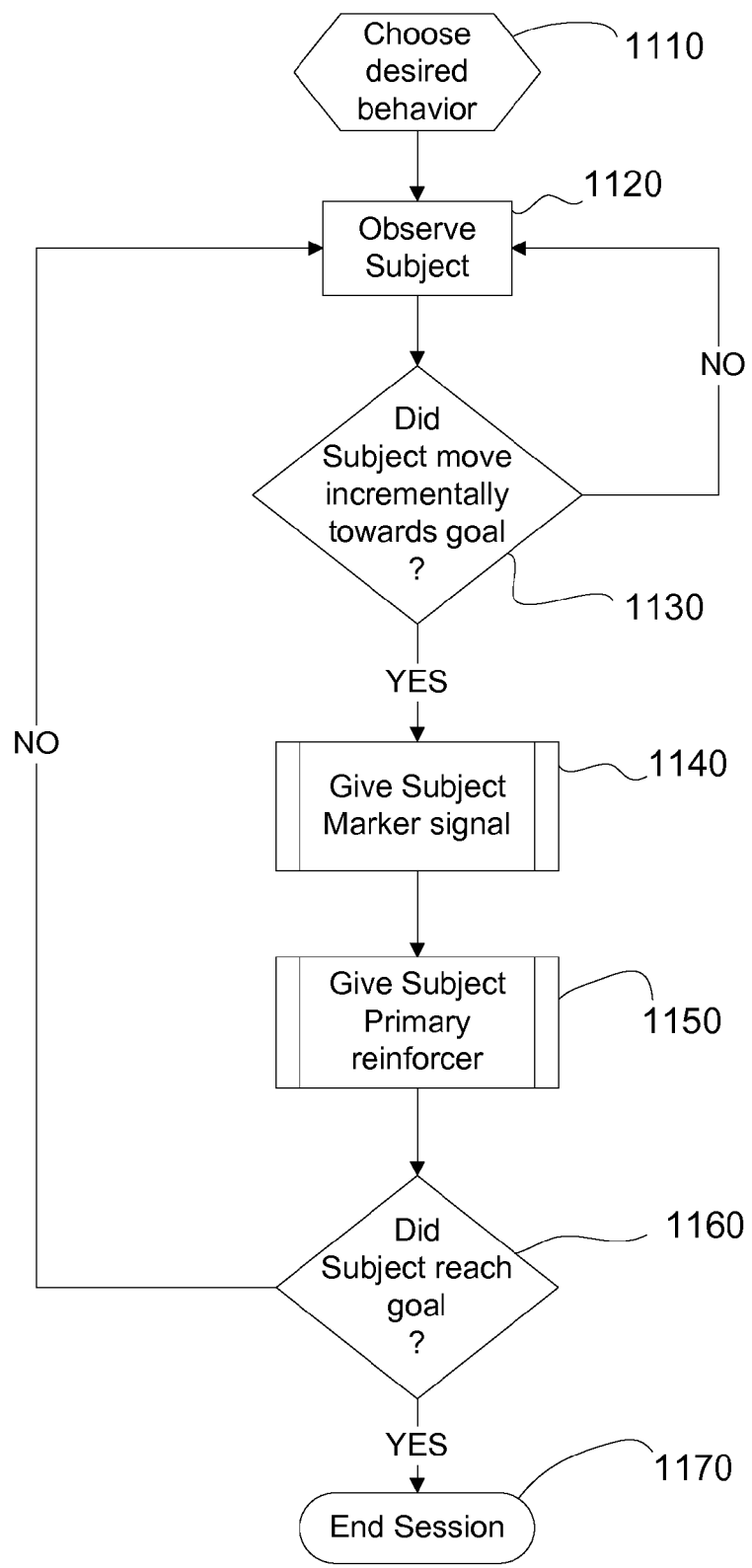
FIG. 11 is a flowchart showing steps by which the user audience can use the embodiments to shape a behavior in the subject.

Referring to FIG. 11, an example of the operation of the embodiments will now be described in using operant conditioning whereby the user audience at the user node shapes a predefined behavior in the subject at the subject node. This can be highly educational, entertaining, or used strictly for rehabilitative purposes. The user audience chooses a predefined behavior 1110 that will serve as a goal for the subject, such as jumping onto a platform, lying down, touching a certain object, using a toilet, etc. The user audience observes the subject as shown in step 1120. If the subject moves incrementally towards the goal as shown in step 1130 (for example moving towards a predefined object), then the user audience gives the subject a marker signal as shown in step 1140.

In the example case where the subject is a child, as in an educational classroom setting, the primary reinforcer used can be a piece of candy or the like handed out by the teacher.

In the example case where the subject is an adult in an entertainment setting, as in an entertainment venue, the primary reinforcer used can be a free drink, hot dog, or a free ticket or the like.

In the example case of a therapeutic setting, the goal behavior selected by the user audience (which might in that case be a single therapist, teacher, psychologist or the like) can be a self-feeding, self-dressing behavior or the like. The goal behavior could also be selected as one that is incompatible with an undesirable behavior. For example, if the subject acts self-injuriously by striking himself with a food tray, the goal behavior chosen for the subject might be to place the food tray in a certain position on a table.

In the case where the example subject is an animal, upon hearing the amplified marker signal at the subject node, a handler located there (not shown) can provide the subject animal with a primary reinforcer such as a food treat as shown in step 1150. As was shown in prior embodiments, this can also be done through both remote and/or automated means (see FIGS. 8A-8D).

As discussed in the Introductory Glossary under "Variable Reinforcement", the frequency and amount of the primary reinforcer described in step 1150 can be varied, such that on occasion the subject is given, for example, a large amount and/or special kind of food treat, a highly desired "jackpot". This unpredictability adds to the excitement and enthusiasm of the subject and so the results are inherently surprising and unexpected.

If the subject has not yet achieved the selected goal behavior, then as shown by steps 1160 & 1120 the subject is again observed as it operantly offers behaviors to make the marker signal occur. If the subject again moves incrementally towards the goal, the marker signal is again given with the subsequent delivery of the primary reinforcer. In this manner, the subject is reinforced for successive, increasingly accurate approximations of the chosen desired behavior. This observation and signaling process continues until the determination is made that the behavior is fully shaped and the subject has reached the goal, as shown in step 1160 and the end of the session shown by step 1170.

Figure 12:
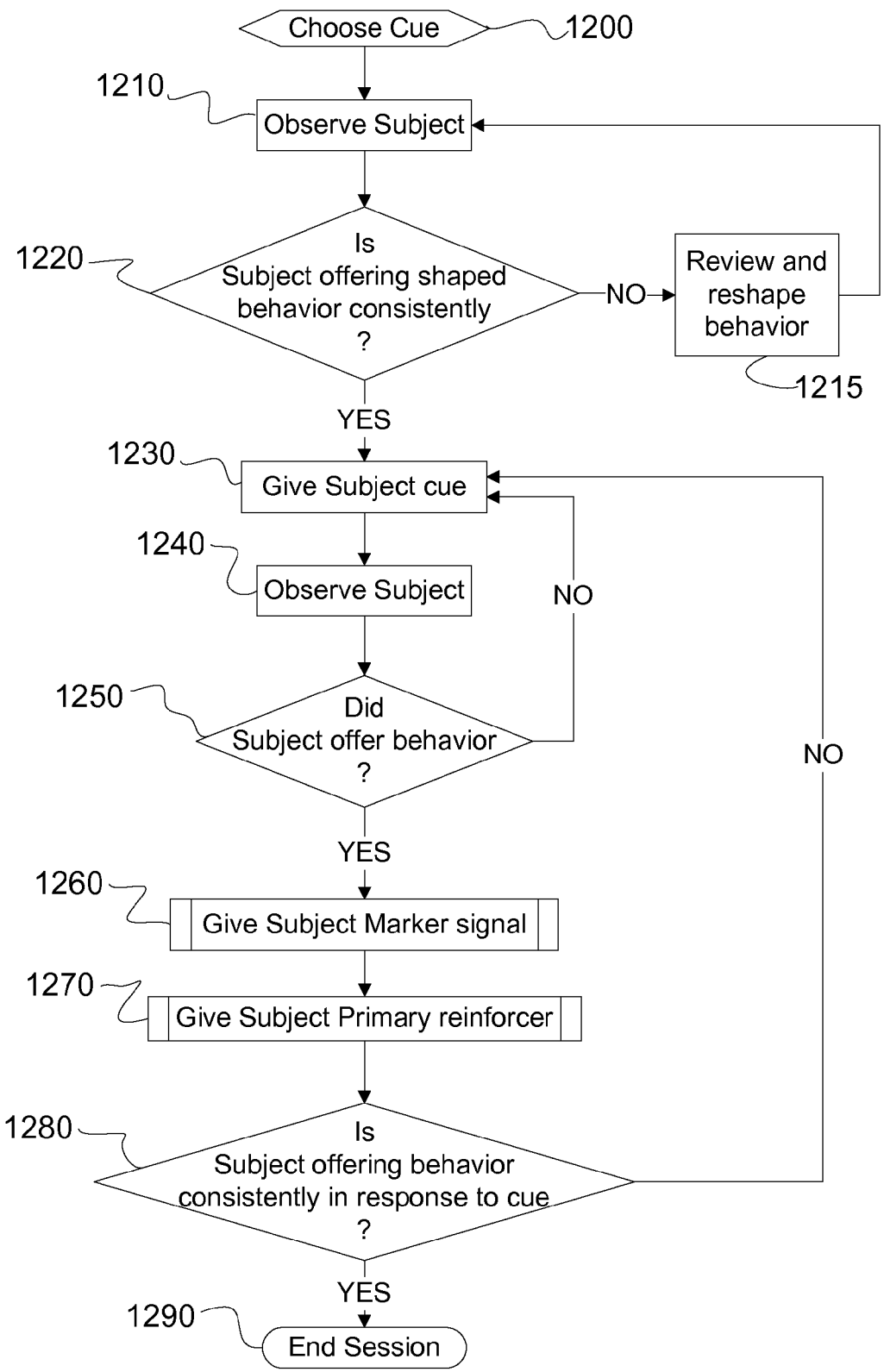
FIG. 12 is a flowchart showing steps by which the user audience can use the embodiments to shape a behavior in the subject under cue control.
Figure 13:
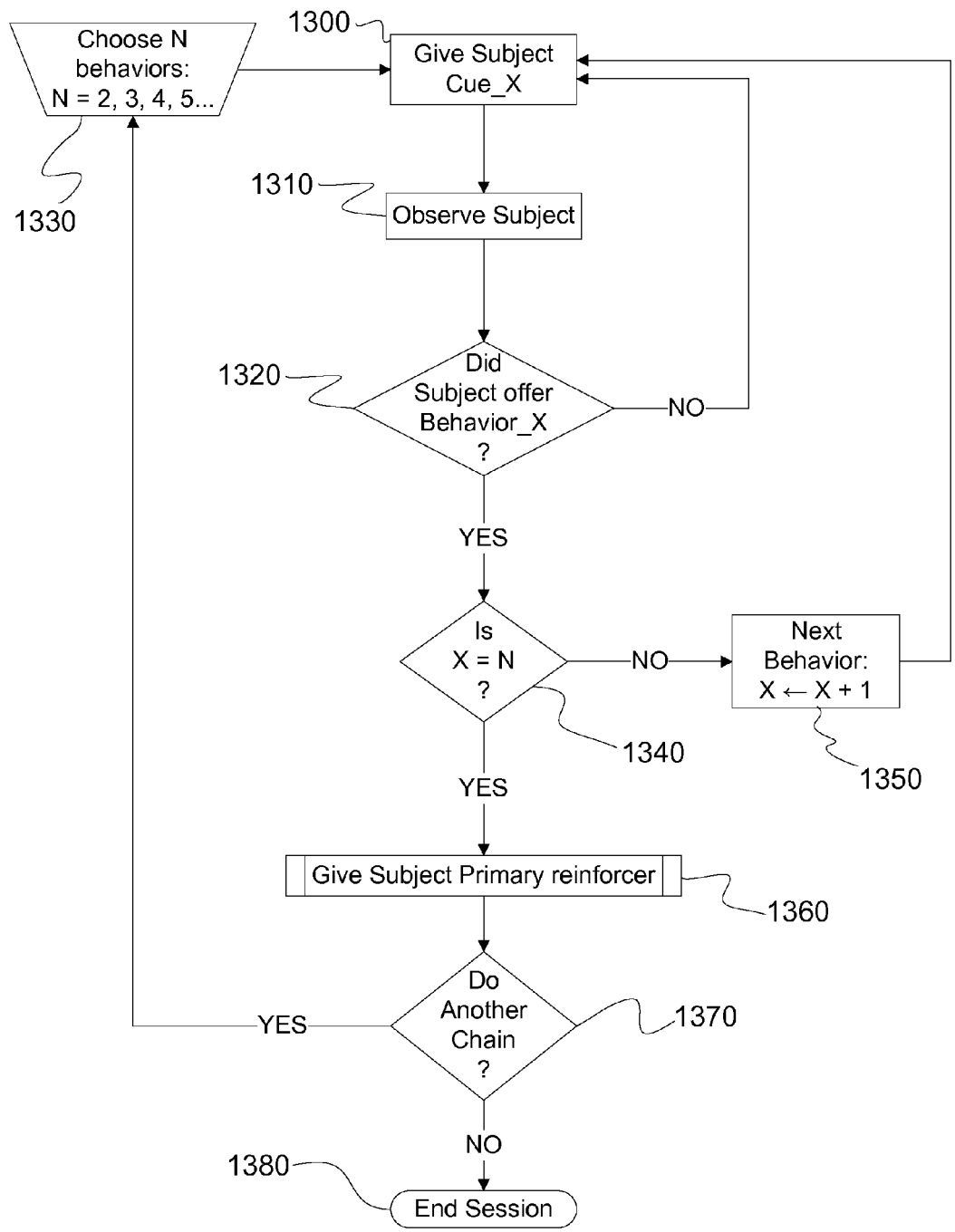
FIG. 13 is a flowchart showing the steps by which the user audience can use the embodiments to shape and/or demonstrate behavior chains.

Referring to FIG. 12, an example of the operation of the embodiments will now be described in using operant conditioning to shape a behavior in the subject to be under cue control.

As shown in step 1200, the user audience chooses or selects a predefined verbal cue (such as "SIT" or "JUMP", for example) to be associated with a previously shaped behavior. The user audience observes the subject as shown in step 1210. As indicated in step 1220, if the subject is not offering the shaped behavior consistently then the behavior should be reviewed or reshaped as shown in step 1215. If the subject is offering the desired behavior consistently so as to earn reinforcements, then the subject is given the chosen cue as shown in step 1230. As shown in step 1240 the subject is observed and if the subject does not offer the desired behavior then the cue is given again shown by step 1250. If the subject does offer the behavior, the user audience gives the subject the marker signal as shown in step 1260.

As shown in step 1270, the primary reinforcer is given responsive to the marker signal. In the example case where the subject is a child, as in an educational classroom setting, the primary reinforcer used can be a piece of candy or the like handed out by the teacher. In the example case where the subject is an adult in an entertainment setting, as in an entertainment venue, the primary reinforcer used can be a free drink, hot dog, or a free ticket or the like. In the case where the example subject is an animal, upon hearing the amplified marker signal at the subject node, a handler located there (not shown) can provide the subject animal with a primary reinforcer such as a food treat or as was shown in prior embodiments, this can also be done through both remote and/or automated means (see FIGS. 8A-8D).

As discussed in the Introductory Glossary under "Variable Reinforcement", the frequency and amount of the primary reinforcer described in step 1270 can be varied, such that on occasion the subject is given, for example, a large amount and/or special kind of food treat, a highly desired "jackpot". This unpredictability adds to the excitement and enthusiasm of the subject and so the results are inherently surprising and unexpected.

As shown in step 1280, this process of reinforcing the subject responsive to performance of the behavior only after the cue is given continues until the determination is made that the subject is offering the desired behavior consistently in response to the cue, at which case the session is ended as shown in step 1290. The subject has effectively learned that the cue is a green light to operantly earn reinforcement for a particular predefined behavior and the behavior is now under cue control. From the subject's point of view since the cue is a green light to earn positive reinforcement, it is a desirable thing and so each cue in and of itself becomes a conditioned reinforcer.

Referring to FIG. 13, an example of the operation of the embodiments will now be described to operantly shape and/or demonstrate a sequence of cued behaviors, also referred to as a behavior chain.

When a subject has learned various behaviors and their associated cues, the embodiments shown can be used to operantly shape and/or demonstrate a sequence of cued behaviors.

Still referring to FIG. 13, as represented by step 1330 the behavior chain can consist of N cues/behaviors. As shown in step 1300, the user audience chooses a predefined cue, shown as Cue_X (for example Cue_1 might be "SIT", Cue_2 might be "JUMP", Cue_3 might be "SPLASH", etc.). This cue can be given to a subject as previously described using the example embodiments. The user audience observes the subject as shown in step 1310 to see if it offers the associated Behavior_X in response to Cue_X (i.e., for the example just described, "SIT" would be Behavior_1, "JUMP" would be Behavior_2, "SPLASH" would be Behavior_3, etc.). As shown in step 1320, if the subject does not offer the behavior associated with the cue, the cue is repeated. If the subject does offer the associated behavior, it is given another cue, as shown in steps 1340 and 1350. As discussed, this next cue is serving as a conditioned reinforcer for offering the behavior. If the behavior chain of N cues is complete, the subject is given the primary reinforcer as shown by step 1360. In this way a sequence of cues and associated behaviors can be shaped or demonstrated as a behavior chain. As shown by step 1370, the session is either ended (shown by step 1380) or continued with another, new sequence of N cues and behaviors as shown by step 1330.

As discussed in the Introductory Glossary under "Variable Reinforcement", the frequency and amount of the primary reinforcer described in step 1360 can be varied, such that on occasion the subject is given, for example, a large amount and/or special kind of food treat, a highly desired "jackpot". This unpredictability adds to the excitement and enthusiasm of the subject and so the results are inherently surprising and unexpected.

Additional Modes of Operation

One of the previous example cases of operation of the embodiments was that of shaping a behavior in a therapeutic setting (in which case the user audience might consist of a single therapist, teacher, or psychologist or the like). Additional example modes of operation of the embodiments can be used in such an example, and similar cases as noted below:

Shaping an incompatible behavior—In treating a problem with a subject, it was discussed that an undesirable behavior in the subject could be treated by operantly conditioning an incompatible behavior (this principle could apply to an example case of a subject human adult, human child, or animal as well). The prior example embodiments and operations can be used to shape a predefined behavior, with the selected predefined behavior being incompatible with an undesirable behavior. (An example given was if the subject acts self-injuriously by striking himself with a food tray, the goal behavior chosen for the subject might be to place the food tray in a certain position on a table). The embodiments can be used to not only shape incompatible behaviors, but to shape and bring them under cue control as well. The shaping was described as being done with the marker signal as a precisely timed conditioned reinforcer signal, defined previously more precisely as a conditioned positive reinforcer signal, unless denoted otherwise.

Extinction of undesirable behavior—Another example mode of operation of the embodiments is that of normal operation for desirable behaviors but withholding reinforcement for an undesirable behavior, under the premise that a behavior gone unreinforced will naturally extinguish. The shaping in normal operation is done with the marker signal as a precisely timed conditioned reinforcer signal, defined previously more precisely as a conditioned positive reinforcer signal, unless denoted otherwise.

Using a negative reinforcer—As noted in the introductory glossary, a reinforcer acts to increase the likelihood of a behavior occurring in the future to increase, wherein a positive reinforcer is a presentation (i.e., addition) of something favorable, and wherein a negative reinforcer is a removal (i.e., subtraction) of something unfavorable. The term primary reinforcer has previously been used to denote more precisely a primary positive reinforcer (such as food or a treat) unless denoted otherwise.

As an example of a negative reinforcement, a seatbelt warning buzzer in a car is an unpleasant stimulus which is removed when the driver puts on a seat belt. The behavior of putting on the seat belt is reinforced through the removal of the negative reinforcer (buzzer). For an example case in a therapeutic setting, a negative stimulus may be present: a mentally ill or developmentally challenged subject patient may be restrained in some fashion to protect from dangerous or self-injurious behavior. This restraint may also be present in the example case of a subject animal with a restraining mechanism such as a bit, bridle, harness, or choke collar or the like. The pressure or discomfort of the restraining mechanism is an unpleasant or aversive stimulus, and its removal in response to a selected desired behavior constitutes reinforcement for that behavior (that reinforcement being defined here in operant conditioning terms as negative reinforcement). If the subject has learned to associate a predefined signal with the impending removal of that restraining pressure or discomfort, then that signal is, in operant conditioning terms, a secondary or conditioned reinforcer signal, more precisely here a conditioned negative reinforcer signal. If the marker signal effected by the user audience (possibly a single therapist or the like) is such a conditioned negative reinforcer signal, it can be precisely timed to mark a predefined behavior incompatible with an undesirable behavior (or the absence of the undesirable behavior). The undesirable behavior in the subject or patient can thusly be treated by operant shaping using the present embodiments. For example, using the conditioned negative reinforcer signal as a marker signal, a therapist at the user node effects a signal at the subject node to a subject patient with a problem behavior of thrashing about, signaling that a protective restraint or the like will be removed when the subject patient is sitting (a behavior incompatible with thrashing about) or at other times in the absence of the undesirable behavior. Similarly, as a further example, in the case of a subject animal, a gate can be opened, a restraint released or the like responsive to a conditioned negative reinforcer signal used to mark the absence of an aggressive food begging behavior (or to mark an incompatible behavior such as quietly lying down). The embodiments can be used to not only shape such incompatible behaviors, but to bring them under cue control as well.

Using a punisher—As also noted in the introductory glossary, a punishment is a consequence to a behavior causing the likelihood of that behavior to decrease. The addition of an unpleasant stimulus (a positive punisher) or the subtraction of a pleasant stimulus (a negative punisher) both serve to punish a given behavior in a subject, causing the likelihood of that behavior occurring in the future to decrease.

An example of a negative punisher would be the removal (or subtraction) of attention (i.e., a "timeout").

An example of a positive punisher would be the addition (or presentation) of pain (i.e., a slap on the wrist). An example of a secondary or conditioned signal associated with a positive punisher would be a loud verbalized "NO!". This signal, in operant conditioning terms a conditioned positive punisher, can be used by a user therapist or trainer at the user node, effecting a conditioned positive punisher signal at the subject node. When precisely timed as a marker signal, it could be used to mark an undesirable behavior, such that the likelihood of that behavior occurring in the future is decreased.

CONCLUSION, RAMIFICATIONS, AND SCOPE

While the above description contains many specificities, these should not be construed as limitations on the scope of any embodiment, but as exemplifications of various embodiments thereof.

For example, dual-mode telephone handsets which hand over calls between cellular and Wi-Fi networks could serve the equivalent functions to the telephone and Internet Protocol networking means previously described. Again similarly, an analog camera connected to a video capture card in a computer would serve the equivalent function as the digital IP network camera previously described.

Many other ramifications and variations are possible within the teachings of the various embodiments. As is known in the art, several means can be embodied by one and the same item of hardware with associated or embedded software or firmware. Many alterations and modifications may be made by those having ordinary skill in the art without departing from the spirit and scope of the invention.

The definitions of the words or elements of the following claims are, therefore, defined in this specification to include not only the combination of elements which are literally set forth, but all equivalent structure, materials or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include that which is specifically illustrated and described above, that which is conceptually equivalent, that which can be obviously substituted, and that which incorporates the essential idea of the invention as disclosed by its several embodiments.

Markush language as used herein encompasses combinations of the individual Markush group members, unless otherwise indicated.

I claim:

1. A distributed operant conditioning system for interactive uses by a user audience such as in educational, entertainment, and therapeutic behavioral modification settings, comprising:

(a) a user node input network link configured to receive real time image data from a subject node;
   wherein a subject at the subject node has associated a conditioned reinforcer with a primary reinforcer;
(b) a display, operatively connected to the user node input network link, the display configured to present image data of the subject to a user audience;
(c) a user interface configured to receive user input and effectuate a predefined operant conditioning signal responsive to the user input;
   wherein the user input is responsive to an observation by the user audience in the real time image data of operantly emitted behaviors of the subject trending towards a predefined behavior;
   wherein the operant conditioning signal is a conditioned reinforcer; and
(d) a user node output network link, operatively connected with the user interface, configured to transmit the operant conditioning signal to the subject node.

2. The system of claim 1, further comprising:
a user interface operable to receive user input and effectuate predefined cue signals responsive to said user input, wherein the user interface is operatively connected with a network link and operable to transmit the predefined cue signals.

3. The system of claim 1, wherein:
the user interface is at least one of the devices selected from the group consisting of a switching device, a computing device, and a telephone device.

4. The system of claim 1, wherein:
the user node input network link is configured to interconnect with an Internet Protocol network.

5. The system of claim 1, wherein:
the user node input network link is configured to interconnect with a telephone network.

6. The system of claim 1, wherein:
the user node output network link is configured to interconnect with an Internet Protocol network.

7. The system of claim 1, wherein:
the user node output network link is configured to interconnect with a telephone network.

8. The system of claim 1, wherein:
the user node output network link is configured to be operable for wireless communication.

9. The system of claim 1, wherein:
the conditioned reinforcer is selected from the group consisting of conditioned positive reinforcer signals and conditioned negative reinforcer signals.

10. A distributed operant conditioning system for interactive uses by a user audience such as in educational, entertainment, and therapeutic behavioral modification settings, comprising:
(a) a subject node input network link configured to receive a predefined operant conditioning signal from a user audience at a user node;
   wherein the operant conditioning signal is responsive to an observation by a user audience at the user node of operantly emitted behaviors of a subject trending towards a predefined behavior; and
   wherein the subject has associated a conditioned reinforcer with a primary reinforcer; and
   wherein the operant conditioning signal is a conditioned reinforcer;
(b) a transducer operatively connected to the subject node input network link, the transducer responsive to the operant conditioning signal and configured to effectuate an indicium of the operant conditioning signal to the subject;
(c) camera means positioned to capture real time image data of the subject; and
(d) a subject node output network link, operatively connected with the camera means, configured to transmit the real time image data to the user node.

11. The system of claim 10, further comprising:
a network link operable to receive predefined cue signals from a user audience, wherein said network link is operatively connected to a transducer, the transducer responsive to the predefined cue signals and operable to effectuate indicia of the cue signals to a subject.

12. The system of claim 10, wherein:
said indicium is effectuated to the subject by at least one of the sensory modes selected from the group consisting of audition, vision, chemoreception, and electroreception.

13. The system of claim 10, wherein:
the subject node input network link is configured to interconnect with an Internet Protocol network.

14. The system of claim 10, wherein:
the subject node input network link is configured to interconnect with a telephone network.

15. The system of claim 10, wherein:
the subject node input network link is configured to be operable for wireless communication.

16. The system of claim 10, wherein:
the subject node output network link is configured to interconnect with an Internet Protocol network.

17. The system of claim 10, wherein:
the subject node output network link is configured to interconnect with a telephone network.

18. The system of claim 10, further comprising:
means to deliver a primary reinforcer to the subject, wherein the primary reinforcer is delivered responsive to the operant conditioning signal.

19. The system of claim 10, wherein:
the conditioned reinforcer is selected from the group consisting of conditioned positive reinforcer signals and conditioned negative reinforcer signals.

20. A method for distributed operant conditioning for interactive uses by a user audience such as in educational, entertainment, and therapeutic behavioral modification settings, comprising:
(a) receiving real time image data of a subject from a subject node;
   wherein the subject has associated a conditioned reinforcer with a primary reinforcer;
(b) displaying the real time image data to a user audience;
(c) receiving user input and generating a predefined operant conditioning signal responsive to the user input;
   wherein the user input is responsive to an observation by the user audience in the real time image data of operantly emitted behaviors of the subject trending towards a predefined behavior; and
   wherein the operant conditioning signal is a conditioned reinforcer;
(d) communicating the operant conditioning signal to the subject node;
(e) effectuating an indicium of the operant conditioning signal to the subject; and
(f) repeating (c)-(e) for each said observation by the user audience in such a manner that said operantly emitted behaviors substantially approximate the predefined behavior.

21. The method of claim 20, further comprising:
(a) generating predefined cue signals;
(b) communicating the cue signals to the subject node; and
(c) effectuating indicia of the cue signals to the subject.

22. The method of claim 20, wherein:
said indicium is effectuated to the subject by at least one of the sensory modes selected from the group consisting of audition, vision, chemoreception, and electroreception.

23. The method of claim 20, wherein:
the operant conditioning signal is communicated using an Internet Protocol network.

24. The method of claim 20, wherein:
the operant conditioning signal is communicated using a telephone network.

25. The method of claim 20, wherein:
the operant conditioning signal is communicated using wireless means.

26. The method of claim 20, further comprising:
delivering a primary reinforcer to the subject, wherein the primary reinforcer is delivered responsive to the operant conditioning signal.

27. The system of claim 20, wherein:
the conditioned reinforcer is selected from the group consisting of conditioned positive reinforcer signals and conditioned negative reinforcer signals.

* * * * *